US011701409B2

(12) United States Patent
Hsu

(10) Patent No.: US 11,701,409 B2
(45) Date of Patent: Jul. 18, 2023

(54) DOSING AND USE OF LONG-ACTING CLR/RAMP AGONISTS

(71) Applicant: Adepthera LLC, Palo Alto, CA (US)

(72) Inventor: Sheau Yu Teddy Hsu, Menlo Park, CA (US)

(73) Assignee: Adepthera LLC, Palo Alto, CA (US)

( * ) Notice: Subject to any disclaimer, the term of this patent is extended or adjusted under 35 U.S.C. 154(b) by 709 days.

(21) Appl. No.: 16/074,330

(22) PCT Filed: Feb. 1, 2017

(86) PCT No.: PCT/US2017/016078
§ 371 (c)(1),
(2) Date: Jul. 31, 2018

(87) PCT Pub. No.: WO2017/139154
PCT Pub. Date: Aug. 17, 2017

(65) Prior Publication Data
US 2021/0000922 A1      Jan. 7, 2021

Related U.S. Application Data

(60) Provisional application No. 62/292,975, filed on Feb. 9, 2016.

(51) Int. Cl.
| | | |
|---|---|---|
| *A61K 38/22* | (2006.01) | |
| *A61K 47/54* | (2017.01) | |
| *A61K 31/704* | (2006.01) | |
| *A61P 9/04* | (2006.01) | |
| *A61P 9/12* | (2006.01) | |

(52) U.S. Cl.
CPC ............ *A61K 38/22* (2013.01); *A61K 31/704* (2013.01); *A61K 47/542* (2017.08); *A61P 9/04* (2018.01); *A61P 9/12* (2018.01)

(58) Field of Classification Search
CPC .. A61K 2300/00; A61K 31/704; A61K 38/22; A61K 38/225; A61K 45/06; A61K 47/542; A61P 9/00; A61P 9/04; A61P 9/10; A61P 9/12; C07K 14/575
See application file for complete search history.

(56) References Cited

U.S. PATENT DOCUMENTS

| | | | |
|---|---|---|---|
| 6,239,107 B1 | 5/2001 | Gozes et al. | |
| 6,268,474 B1 | 7/2001 | Smith et al. | |
| 9,694,051 B2 | 7/2017 | Hsu et al. | |
| 2008/0020978 A1 | 1/2008 | Pegg et al. | |
| 2008/0026995 A1 | 1/2008 | Tosi et al. | |
| 2008/0113411 A1 | 5/2008 | Sheffer et al. | |
| 2008/0207501 A1 | 8/2008 | Erickson et al. | |
| 2008/0274952 A1 | 11/2008 | Soares et al. | |
| 2009/0036364 A1 | 2/2009 | Levy et al. | |
| 2009/0088387 A1 | 4/2009 | Castillio et al. | |
| 2009/0175821 A1 | 7/2009 | Bridon et al. | |
| 2009/0186817 A1 | 7/2009 | Ghosh et al. | |
| 2010/0048871 A1 | 2/2010 | Cho et al. | |
| 2010/0249104 A1 | 9/2010 | Liu et al. | |
| 2011/0190193 A1 | 8/2011 | Stroes | |
| 2013/0281374 A1 | 10/2013 | Levy et al. | |
| 2014/0155329 A1 | 6/2014 | Hsu et al. | |
| 2014/0249299 A1 | 9/2014 | Levy et al. | |

FOREIGN PATENT DOCUMENTS

| | | | |
|---|---|---|---|
| CN | 101035806 A | 9/2007 | |
| CN | 101208099 A | 6/2008 | |
| JP | H11502204 A | 2/1999 | |
| JP | 2002/540216 A | 11/2002 | |
| JP | 2008/507280 A | 3/2008 | |
| JP | 2008/515443 A | 5/2008 | |
| JP | 2014/511862 A | 5/2014 | |
| WO | 1996/029432 A1 | 9/1996 | |
| WO | 2006/082184 A2 | 8/2006 | |
| WO | 2008/022716 A2 | 2/2008 | |
| WO | WO-2009152415 A2 * | 12/2009 | ................ A61P 9/00 |
| WO | 2012/138867 A2 | 10/2012 | |

OTHER PUBLICATIONS

Chia Lin Chang, Development of chimeric and bifunctional antagonists for CLR/RAMP receptors, PLoS One 14(5): e0216996, 2019.*
Takeshi et al. (2002) "Adrenomedullin Inhibits Doxorubicin-Induced Cultured Rat Cardiac Myocyte Apoptosis via a cAMP-Dependent Mechanism" 9-15 Endocrinology, vol. 1 • 143. No. 9. 3515-3521.
Chapter et al., "Chemical modification of Class II G-protein coupled receptor ligands: Frontiers in the developmentof peptide analogs as neuroendocrine pharmacological therapies", Pharmacal Ther, Jan. 2010, pp. 1-33, vol. 125, Issue 1, Elsevier, New York, NY.
Dasgupta et al., "Lipophilization of somatostatin analog RC-160 with long chain fatty acid improves itsantiproliferative and antiangiogenic activity in vitro", Br J Pharmacal, Jan. 2000 pp. 1-9, 129(1 ):1, MacmillanPublishers Ltd, London, United Kingdom.
Gaul T et al., "Enhanced cAMP generation and insulin-releasing potency of two novel Tyr1-modified enzyme-resistant arms of glucose-dependent insulinotropic polypeptide is associated with significant antihyperglycaemic activity in spontaneous obesity diabetes", Biochem J., Nov. 1, 2002, pp. 913-920, 367(Pt 3), Biochemical Society, London, United Kingdom.

(Continued)

*Primary Examiner* — Julie Ha
*Assistant Examiner* — Erinne R Dabkowski
(74) *Attorney, Agent, or Firm* — Pamela J. Sherwood; Bozicevic, Field & Francis LLP

(57) ABSTRACT

Long-acting agonistic analogs for CLR/RAMP receptors are provided that have an extended half-live in vivo. The agonists are delivered to an individual at a dose sufficient to reduce hypertension and ischemic injury, and to reduce cardiotoxicity associated with chemotherapeutic agents.

8 Claims, 5 Drawing Sheets

Specification includes a Sequence Listing.

(56) References Cited

OTHER PUBLICATIONS

Jagadish et al., "Squalene-derived Flexible Linkers for Bioactive Peptides", Bioorg Med Chem Lett, Jun. 15, 2007, pp. 3310-3313, vol. 17, Issue 12, Elsevier, New York, NY.
Kato et al., "Adrenomedullin: A Protective Factor for Blood Vessels", Arterioscler Thromb Vase Bioi, Sep. 1, 2005, pp. 2480-2487, 25, American Heart Association, Dallas, TX.
Knudsen et al., "Potent Derivative of Glucagon-like Peptide-1 with Pharmacokinetic Properties Suitable for OnceDaily Administration", J. Med. Chern., Dec. 3, 1999, pp. 1664-1669, vol. 43, No. 9, Washington, D.C.
Kostel et al., "Purification of a lipid peptide: Method development for Hydrophobic Peptides", Conference abstract presented at ABRF in 1998.
Kubo et al., "Biological properties of adrenomedullin conjugated with polyethylene glycol", Peptides, May 5, 2014, pp. 118-127, 57, Elsevier, Philadelphia, PA.
Kurtzhals, "How to achieve a predictable basal insulin?", Diabetes Metab, 2005, pp. 4S25-4S33, 31(4 Pt 2): Elsevier, Philadelphia, PA.
Li et al., "Adrenomedullin Is Decreased in Preeclampsia Because of Failed Response to Epidermal Growth Factor and Impaired Syncytialization", Hypertension, Nov. 6, 2003, pp. 895-900, 42, American Heart Association, Dallas, TX.
Maletinska et al., "Angiotensin Analogues Palmitoylated in Positions 1 and 4", J. Med. Chem. 1997, pp. 3271-3279,40, American Chemical Society, Washington, D.C.
Meeran et al., "Circulating Adrenomedullin Does Not Regulate Systemic Blood Pressure but Increases PlasmaProlactin after Intravenous Infusion in Humans: A Pharmacokinetic Study", Journal of Clinical Endocrinology and Metabolism, Jan. 1997, pp. 95-100, 82(1), The Endocrine Society,Washington, DC.
Nagaya et al., "Adrenomedullin in the treatment of pulmonary hypertension", Peptides, Nov. 2004, pp. 2013-2018, vol. 25, Issue 11, Elsevier, New York City, NY.
Pennington, "Methods in Molecular Bology", Methods in Molecular Biology, 1994, pp. 171-185, vol. 35 PeptideSynthesis Protocols Ch 8, Site-Specific Chemical Modification Procedures,Humana Press Inc, Totowa, NJ.
Santiago et al., "Comparison of responses to adrenomedullin and adrenomedullin analogs in the mesenteric vascular bed of the cat", Eur J Pharmacal., Jan. 5, 1995, pp. 115-118, 272(1 ). Elsevier, New York City, NY.
Takahash I et al., "Adrenomedullin 2/intermedin in the hypothalamo-pituitary-adrenal axis", J Mol Neurosci, Jun. 11, 2010, pp. 182-192,43 {2), Springer Science & Business Media, LLC, New York, NY.
Wu et al., "Human vasoactive hormone adrenomedullin and its binding protein rescue experimental animals fromshock", Peptides, Feb. 28, 2008, pp. 1223-1230, 29(7), Elsevier, New York City, NY.
Yang et al., "Effects of intermedin1-53 on cardiac function and ischemia/reperfusion injury in isolated rat hearts", Biochemical and Biophysical Research Communications Dec. 22, 2004, pp. 713-719, 327(3), Elsevier, New York City, NY.

\* cited by examiner

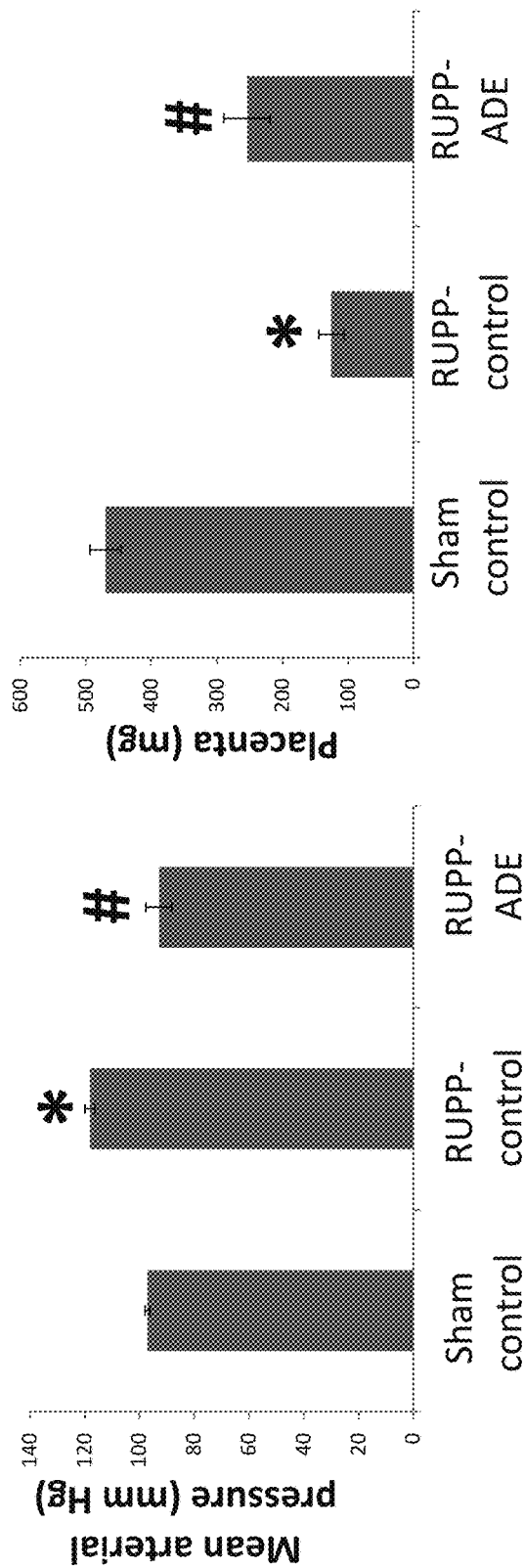
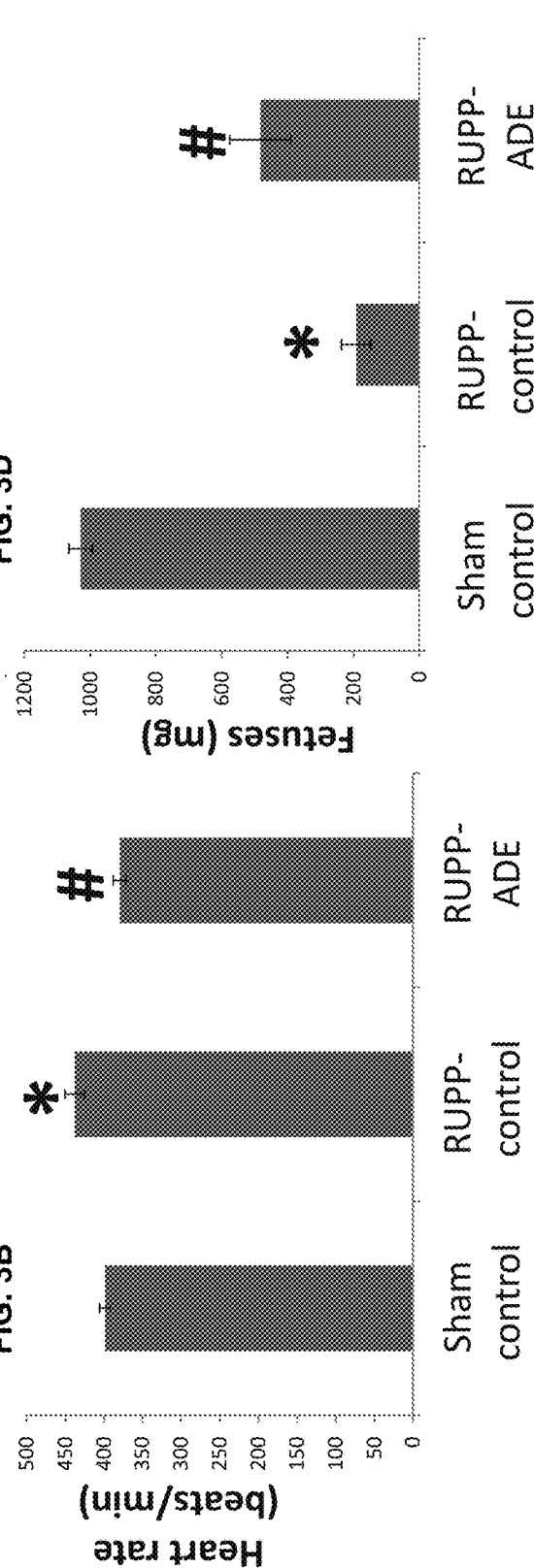

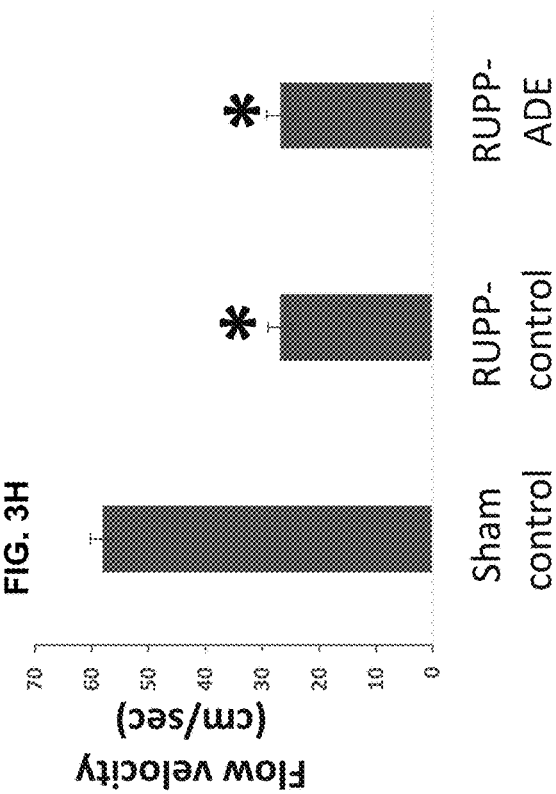
FIG. 3G
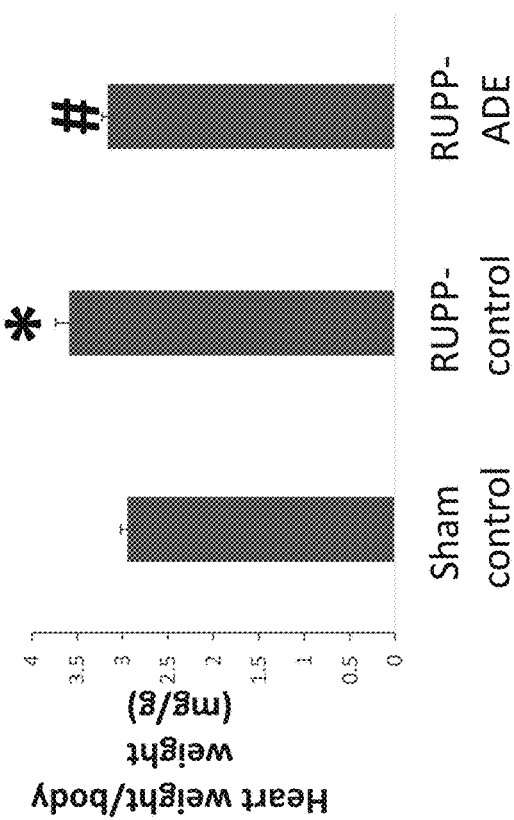
FIG. 3H
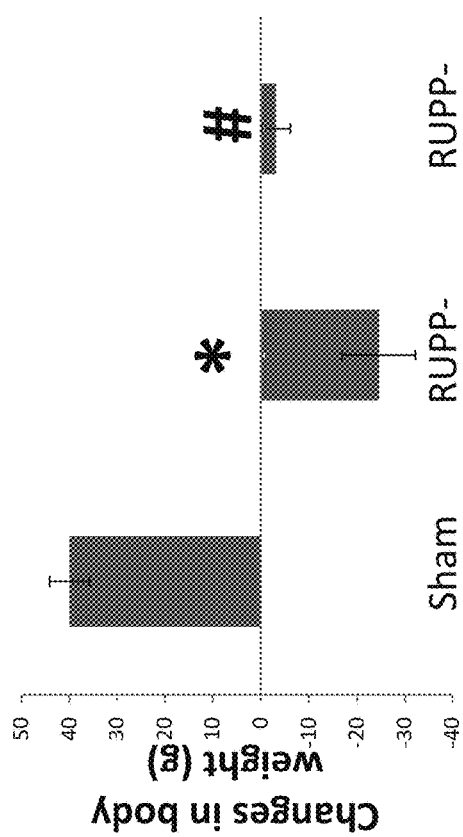
FIG. 3E
FIG. 3F

DOSING AND USE OF LONG-ACTING CLR/RAMP AGONISTS

CROSS REFERENCE

This application claims benefit of PCT Application No. PCT/US2017/016078, filed Feb. 1, 2017, which claims benefit of U.S. Provisional Patent Application No. 62/292,975, filed Feb. 9, 2016, which applications are incorporated herein by reference in their entirety.

INTRODUCTION

Endothelial dysfunction is a leading cause of morbidity and mortality that are associated with micro and macrovascular complications in a variety of life-threatening diseases, including atherosclerosis, heart failure, resistant hypertension, hypertensive crisis, stroke, myocardial infarction, preeclampsia, pulmonary arterial hypertension, and diabetic ulcers (Sanchez-Aranguren et al. (2014) Front Physiol 5:372; Park and Park (2015) J Korean Med Sci 30:1213-1225; Mordi and Tzemos (2014) World J Cardiol 6:824-835). Endothelial dysfunction is an early event along the natural course of these diseases, and represents an important risk factor. The function of vascular endothelium includes the synthesis of substances that modulate vascular tone, the inhibition of platelet aggregation, and control of proliferation of vascular cells. Damage to the endothelium can lead to reduced nitric oxide production, increased endothelium-derived contracting factors, and breakdown of endothelial barriers, leading to vasoconstriction, thrombosis, increased vascular resistance, vascular leakage, and edema. This is clinically manifested as hypertension, atherosclerosis, left ventricular cardiomyopathy, ischemic ulcers, and renal impairment.

Although improvement in health care in the last two decades has dramatically improved the outcomes of patients with some of these diseases, the progression of most of these diseases cannot be effectively prevented due to the lack of treatment that can target endothelial dysfunction specifically. For example, currently the standard care for preeclampsia, a hypertensive disorder during pregnancy, is prophylactic measures, including bedrest, intensive prenatal care, antibiotics, and anti-seizure medications. However, there is no evidence that any of these measures are effective at delaying labor by more than a couple of days in preeclamptic women. The only "cure" for the disease is delivery of the baby (Pennington et al. (2012) Dis Model Mech 5:9-18; Fisk and Atun (2008) PLoS Med 5:e22). As a result, patients with preeclampsia face serious long-term morbidities and high mortality rate of both the mother and the fetus, and nearly 100,000 preterm babies are born in the US annually due to preeclampsia. On the other hand, patient with resistant hypertension, which occurs in ~10% of patients who received standard hypertension treatment suffer twice the probability of developing myocardial infarction, stroke and a variety of cardiovascular diseases and higher mortality rates when compared to patients with controlled blood pressure despite the use of 4-5 different classes and anti-hypertensive therapeutics (Muntner et al. (2014) Hypertension 64:1012-1021; Smith et al. (2014) J Hypertens 32:635-643; Calhoun et al. (2014) Hypertension 63:451-458). Likewise, there is a complete lack of therapeutics that can target endothelial dysfunction in the lymphatic system. As a result, patients with lymphatic disorders such as obesity- and breast cancer treatment-induced lymphedema suffer life-long struggle with secondary lymphedema.

New approaches that can ameliorate endothelial dysfunction and restore normal vascular functions in patients with preeclampsia, resistant hypertension, hypertensive crisis, breast cancer treatment-induced lymphedema, or other endothelial dysfunction-associated diseases are urgently needed.

Recent studies have shown that (1) two endocrine hormones, adrenomedullin (ADM) and intermedin (IMD), or adrenomedullin 2 (ADM2), are major regulators of vasotone and endothelial barrier integrity, and (2) have potent stimulatory effects on the proliferation of blood and lymphatic endothelial cells that serve as starter materials for blood vessels, angiogenesis, and vascular remodeling (Shindo et al. (2001) Circulation 104:1964-1971; Ichikawa-Shindo et al. (2008) J Clin Invest 118:29-39; Koyama et al. (2013) Circulation 127:842-853). ADM and IMD belong to a peptide family that also includes calcitonin gene-related peptides (α- and β-CGRP). These peptides are structurally similar and signal through receptor complexes consisting of two transmembrane components, the calcitonin receptor-like receptor (CLR) and one of the three receptor activity-modifying proteins (RAMP1, 2, and 3) (Christopoulos et al. (1999) Mol. Pharmacol. 56:235-242; Poyner et al. (2002) Pharmacol. Rev. 54:233-246; McLatchie et al. (1998) Nature 393:333-339). Whereas CGRPs mainly act through the CLR/RAMP1 receptor, ADM has high affinity for CLR/RAMP2 and 3 receptors. On the other hand, IMD is a weak ligand and exhibits no distinct preference for the three CLR/RAMP receptors.

Although ADM and IMD were first characterized as potent vasotone regulators, subsequent investigations have revealed that ADM, IMD, and CGRPs play essential roles in the regulation of peripheral vascular resistance, vascular permeability, cardiac output, neuronal cell survival, and renal glomerular filtration.

Studies using mutant mice deficient for CGRP or ADM have indicated that, in different systems, CLR plays important roles in the regulation of cardiovascular morphogenesis, sensory neurotransmission, inflammatory reactions, nociceptive behavior, and glucose homeostasis. Thus, the physiological functions of peptides in this family are determined by receptor-binding specificity and the tissue expression profiles of individual ligands.

Peptide hormones are of great interest for clinical use and the development of therapies, including treatment of atherosclerosis, heart failure, resistant hypertension, refractory hypertension, stroke, myocardial infarction, preeclampsia, pulmonary arterial hypertension, secondary lymphedema and diabetic ulcers and maintenance of cardiovascular homeostasis. Although earlier studies suggested that ADM family peptides are potential therapeutic candidates for the treatment of a variety of endothelial dysfunction-associated diseases; however, intravenously administered wild-type peptides are rapidly cleared, and can lead to compensated tachycardia at pharmacological dosages.

RELATED PUBLICATIONS

Hay and Smith (2001) Trends Pharmacol. Sci. 22:57-59; Li et al. (2013) J Clin Invest 123:2408-2420; Fritz-Six et al. (2008) J Clin Invest 118:40-50; Dackor et al. (2006) Mol Cell Biol 26:2511-2518; Caron and Smithies (2001) PNAS 98:615-619; Yoshizawa et al. (2013) Hypertension 61:341-351; Koyama et al. (2015) J Atheroscler Thromb 22:647-

653; Shindo et al. (2013) *Curr Protein Pept Sci* 14:347-357; Niu et al. (2004) *Circulation* 109:1789-1794) and Shindo et al. (2001) *Circulation* 104:1964-197 discuss the importance of adrenomedullin in the vasculature. The role of a CGRP is discussed by Zhang et al. (2001) *Pain* 89:265-273; Salmon et al. (1999) *Neuroreport* 10:849-854; and Salmon et al. (2001) *Nat. Neurosci.* 4:357-358. The role of amylin is discussed by Mulder et al. (2000) *Am. J. Physiol. Endocrinol. Metab.* 278:E684-691.

GenBank entry AF529213.

SUMMARY OF THE INVENTION

Methods of use for long-acting CLR/RAMP receptor agonists are provided herein. In some embodiments, the long-acting CLR/RAMP receptor agonists are delivered to an individual at a dose sufficient to reduce hypertension and ischemic injury, particularly hypertension associated with pregnancy, e.g. pre-eclampsia, and hypertensive crisis. The analog may be delivered by an injection or infusion, including continuous infusion. The dose can be sufficient to reduce one or more of mean arterial pressure, tachycardia, ischemic injury, organ toxicity, end organ failure, and cardiac hypertrophy.

In other embodiments, co-administration of a long-lasting CLR/RAMP receptor agonist is shown to reduce cardiotoxicity associated with chemotherapeutic agents, including without limitation anthracyclines.

Long-acting CLR/RAMP receptor agonists useful in the methods of the invention provide for the biological activities of adrenomedullin, intermedin, or CGRPs, including acting as ligand for the calcitonin receptor-like receptor/RAMP receptors, but have a substantially longer in vivo half-life when compared to the native polypeptide. Such analogs provide for an in vivo effectiveness that lasts at least 2-fold longer in duration than the native peptide, and may be 5-fold longer, 10-fold longer, 20-fold longer, or more. Of particular interest is the hypotensive effect, where a single dose of the analog peptide effective in reducing systolic blood pressure, or mean arterial pressure, by at least about 10% is effective in maintaining reduced blood pressure for at least about 1 hour, at least about 2 hours, at least about 3 hours, at least about 4 hours, or more.

The long-acting CLR/RAMP receptor agonists comprise a biologically active adrenomedullin, intermedin, or chimeric adrenomedullin/intermedin polypeptide that has been modified at the N-terminus. N-terminal modifications of interest include conjugation to a fatty acid, usually a C4 to C30 fatty acid, which may be unsaturated or saturated, or a polyethylene glycol molecule. Fatty acids of interest include, without limitation, palmitic acid; stearic acid; arachidic acid; lauric acid; myristic acid; myristoleic acid; palmitoleic acid; sapienic acid; oleic acid; linoleic acid; α-linolenic acid; arachidonic acid; eicosapentaenoic acid; erucic acid; docosahexaenoic acid; etc. The amino terminus may be modified by the addition of a lysine residue for conjugation of the fatty acid.

In its many embodiments, the present invention relates to a novel method of treating a patient with ischemic injury. A method of treatment, prevention, inhibition or amelioration of one or more diseases associated with CLR/RAMP receptor and related to ischemic injury using long-acting CLR/RAMP receptor agonists is provided.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 2A In a low-dose treatment study, pregnant rats received 3.3 µg/kg/hr of the long-acting stable analog, or saline for four days. When compared to the sham controls, RUPP control rats have significantly increased mean arterial pressure. FIG. 2B Average placenta weight of sham controls was 510±26 mg. The placenta weight was significantly reduced in both RUPP-control and the RUPP-stable analog.

FIG. 3A-3H. A low dosage of the long-acting stable analog has minimal effects on restricted uterine perfusion pressure (RUPP)-induced hypertension or fetal/placental development. The RUPP surgery led to significant increases of mean arterial pressure FIG. 3A, and decreases of fetus and placenta weights FIG. 3B in pregnant rats. However, the low-dose stable analog treatment has minimal effects on these RUPP-induced adverse effects. FIG. 3. A high dosage of long-acting stable analog has significant protective effects on a variety of RUPP-induced adverse effects. The RUPP surgery led to significant increases of mean arterial pressure FIG. 3A and heart rate FIG. 3B, and decreases of fetus weight FIG. 3C, placenta weight FIG. 3D and body weight FIG. 3E. The RUPP treatment also led to cardiac hypertrophy FIG. 3F. Importantly, the high-dose analog treatment significantly reduced the RUPP-induced adverse effects on mean arterial pressure, heart rate, fetus weight, placenta weight, body weight, and heart weight FIG. 3A-3F. Doppler measurements showed that the blood flow velocity above the constriction sites is the same among treatment groups FIG. 3G. On the other hand, the blood flow velocity below the constriction sites was reduced by more than 50% in RUPP-control and RUPP-ADE animals FIG. 3H. Significant differences between the sham control and RUPP-control groups are indicated by asterisks (P<0.05). Significant differences between the RUPP-control and RUPP-ADE groups are indicated by # symbols (P<0.05).

DESCRIPTION OF THE SPECIFIC EMBODIMENTS

Figure 1A:
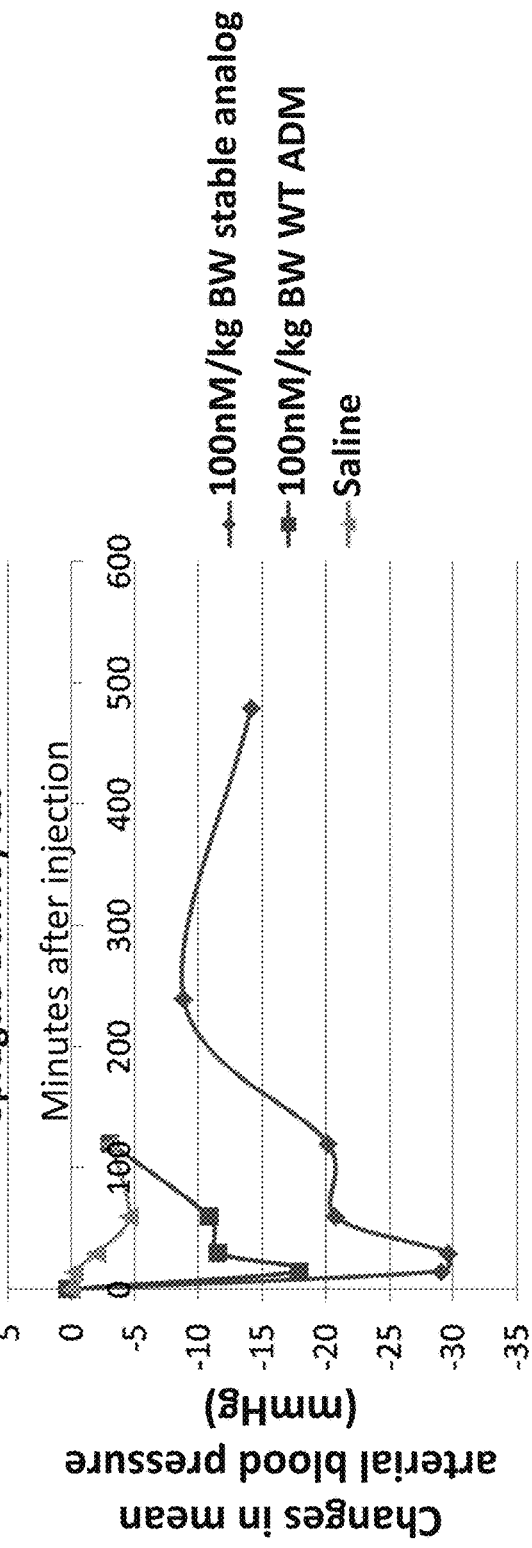
FIG. 1A-1B. Bolus IP injection of the long-acting CLR/RAMP receptor agonist (i.e., a long-acting ADM analog SEQ ID NO: 2; labeled as "stable analog" in Figures) led to a sustained reduction of blood pressure for 4 hr in normal pregnant Sprague Dawley rats, whereas the hypotensive effects of wild-type ADM disappeared within 2 hr FIG. 1A. Administration of a low dose of the long-acting stable analog (30 nmoles/kg) consistently reduced blood pressure for 2 hr in pregnant Sprague Dawley rats. In contrast, the hypotensive effects of the long-acting stable analog lasted over 8 hr in pregnant SHR rats FIG. 1B.

The invention provides novel polypeptide analogs of adrenomedullin, which is a member of the calcitonin peptide hormone family. Adrenomedullin is a ligand for the calcitonin receptor-like receptor. The ADM gene encodes for a preprohormone, which is posttranslationally modified to generate 2 biologically active peptides: adrenomedullin and proadrenomedullin N-terminal 20 peptide (PAMP). Adrenomedullin consists of 52 amino acids, has 1 intramolecular disulfide bond, and shows slight homology with the calcitonin gene-related peptide. The precursor, called preproadrenomedullin, is 185 amino acids long. See Genbank reference NM_001124, herein specifically incorporated by reference. The precursor polypeptide (SEQ ID NO:1) has the amino acid sequence:

```
MKLVSVALMYLGSLAFLGADTARLDVASEFRKKWNKWALSRGKRELRMSS
SYPTGLADVKAGPAQTLIRPQDMKGASRSPEDSSPDAARIRVKRYRQSMN
NFQGLRSFGCRFGTCTVQKLAHQIYQFTDKDKDNVAPRSKISPQGYGRRR
RRSLPEAGPGRTLVSSKPQAHGAPAPPSGSAPHFL.
```

For the purposes of the invention, the term "adrenomedullin peptide" may refer to any active peptide derived from the adrenomedullin precursor peptide, unless otherwise specified. Of particular interest are hypotensive peptides. The active peptide includes, without limitation, the long-acting CLR/RAMP receptor agonist having the amino acid sequence (SEQ ID NO:2, or long-acting adrenomedullin peptide) K(mod)GCRFGTCTVQKLAHQIYQFTDKDKDNVAPRSKIS-PQGY, where the lysine at residue 1 is modified, e.g. by attachment of a lipid or other group, or having the amino acid sequence of SEQ ID NOS: 3-34 (Table 1).

A structure of the long acting peptide is shown in structure I.

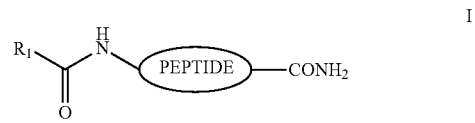

where $R_1$ is a linear or branched $C_3$-$C_{100}$ alkyl; preferably a $C_4$-$C_{30}$ alkyl optionally substituted with halo, hydroxy, alkoxy, amino, alkylamino, dialkylamino, sulfate, or phosphate, and which may by saturated, or mono- or di-unsaturated, e.g. 18:0, 24:0 and 24:1. Fatty acids of interest include, without limitation, palmitic acid; stearic acid; arachidic acid; lauric acid; myristic acid; myristoleic acid; palmitoleic acid; sapienic acid; oleic acid; linoleic acid; α-linolenic acid; arachidonic acid; eicosapentaenoic acid; erucic acid; docosahexaenoic acid; etc.

TABLE 1

| List of long-acting CLR/RAMP receptor agonists | |
|---|---|
| Ace-K(Pal)GCRFGTCTVQKLAHQIYQFTDKDKDNVAPRSKISPQGY-NH2 | (SEQ ID NO: 2) |
| miniPEG-K(PAL)GCRFGTCTVQKLAHQIYQFTDKDKDNSAPVDPSSPHSY-NH2 | (SEQ ID NO: 3) |
| miniPEG-K(PAL)GCRFGTCTVQKLAHQIYQFTPAGRQDSAPVDPSSPHSY-NH2 | (SEQ ID NO: 4) |
| Pal-KGCRFGTCTVQKLAHQIYQFTDKDKDNSAPVDPSSPHSY-NH2 | (SEQ ID NO: 5) |
| Pal-KGCRFGTCTVQKLAHQIYQFTPAGRQDSAPVDPSSPHSY-NH2 | (SEQ ID NO: 6) |
| Ace-K(PAL)GCRFGTCTVQKLAHQIYQFTDKDKDNSAPVDPSSPHSY-NH2 | (SEQ ID NO: 7) |
| Ace-K(PAL)GCRFGTCTVQKLAHQIYQFTPAGRQDSAPVDPSSPHSY-NH2 | (SEQ ID NO: 8) |
| Pal-KGCRFGTCTVQKLAHQIYQFTDKDKDNVAPVDPSSPHSY-NH2 | (SEQ ID NO: 9) |
| Pal-KGCRFGTCTVQKLAHQIYQFTDKDKQDSAPVDPSSPHSY-NH2 | (SEQ ID NO: 10) |
| Pal-KGCRFGTCTVQKLAHQIYQFTDKGRQDSAPVDPSSPHSY-NH2 | (SEQ ID NO: 11) |
| Pal-K(Pal)GCRFGTCTVQKLAHQIYQFTDKDKDNSAPVDPSSPHSY-NH2 | (SEQ ID NO: 12) |
| Pal-KTKKTLRTGCRFGTCTVQKLAHQIYQFTDKDKDNSAPVDPSSPHSY-NH2 | (SEQ ID NO: 13) |
| Ace-TK(Pal)KTLRTGCRFGTCTVQKLAHQIYQFTDKDKDNSAPVDPSSPHSY-NH2 | (SEQ ID NO: 14) |
| Pal-KTKKTLRTGCRFGTCTVQKLAHQIYQFTDKDKDNVAPVDPSSPHSY-NH2 | (SEQ ID NO: 15) |
| Ace-TK(Pal)KTLRTGCRFGTCTVQKLAHQIYQFTDKDKDNVAPVDPSSPHSY-NH2 | (SEQ ID NO: 16) |
| miniPEG-TK(Pal)KTLRTGCRFGTCTVQKLAHQIYQFTDKDKDNVAPVDPSSPHSY-NH2 | (SEQ ID NO: 17) |
| miniPEG-K(PAL)CRFGTCTVQKLAHQIYQFTDKDKDNSAPVDPSSPHSY-NH2 | (SEQ ID NO: 18) |
| Pal-KCRFGTCTVQKLAHQIYQFTDKDKDNSAPVDPSSPHSY-NH2 | (SEQ ID NO: 19) |
| Pal-GCRFGTCTVQKLAHQIYQFTDKDKDNSAPVDPSSPHSY-NH2 | (SEQ ID NO: 20) |
| miniPEG-K(PAL)GCRFGTCTVQKLAHQIYQFTDKDKDSAPVDPSSPHSY-NH2 | (SEQ ID NO: 21) |
| miniPEG-K(PAL)GCRFGTCTVQKLAHQIYQFTDKSAPVDPSSPHSY-NH2 | (SEQ ID NO: 22) |

TABLE 1-continued

List of long-acting CLR/RAMP receptor agonists

| | |
|---|---|
| miniPEG-K(PAL)GCRFGTCTVQKLAHQIYQFTDKDSAPVDPSSPHSY-NH2 | (SEQ ID NO: 23) |
| miniPEG-K(PAL)GCRFGTCTVQKLAHQIYQFTPAGRQDSAPVDPSSPHSY-NH2 | (SEQ ID NO: 24) |
| miniPEG-K(PAL)GCRFGTCTVQKLAHQIYQFTDKDKDNVAPVDPSSPHSY-NH2 | (SEQ ID NO: 25) |
| miniPEG-K(PAL)GCRFGTCTVQKLAHQIYQFTDKDKQDSAPVDPSSPHSY-NH2 | (SEQ ID NO: 26) |
| K(Pal)GCVLGTCQVQNLSHRLWQLMGPAGRQDSAPVDPSSPHSY-NH2 | (SEQ ID NO: 27) |
| Pal-KGCRFGTCTVQKLAHQIYQFTDKDSAPVDPSSPHSY-NH2 | (SEQ ID NO: 28) |
| miniPEG-K(PAL)GCRFGTCTVQKLAHQIYQFTDKDKDNVAPRSKISPQGY-NH2 | (SEQ ID NO: 29) |
| miniPEG-K(PAL)TKKTLRTGCRFGTCTVQKLAHQIYQFTDKDKDNVAPRSKISPQGY-NH2 | (SEQ ID NO: 30) |
| miniPEG-K(PAL)GCRFGTCTVQKLAHQIYQFTDKDKDNVDPSSPHSY-NH2 | (SEQ ID NO: 31) |
| miniPEG-K(PAL)GCRFGTCTVQKLAHQIYQFTDKDVAPRSKISPQGY-NH2 | (SEQ ID NO: 32) |
| Pal-KGCRFGTCTVQKLAHQIYQFTDKDVAPRSKISPQGY-NH2 | (SEQ ID NO: 33) |
| Pal-KGCRFGTCTVQKLAHQIYQFTDKDAPVDPSSPHSY-NH2 | (SEQ ID NO: 34) |

Adrenomedullin (ADM) and intermedin are ligands of the CLR/RAMP receptors, and activates the receptor upon binding. Activation by adrenomedullin or intermedin results in the vascular system effects including lowering of blood pressure, vasodilation, increase of vascular stability and reduction of ischemic injury. Thus, adrenomedullin and intermedin signal through the CLR/RAMP receptors to regulate peripheral vasodilation-related processes, and they have beneficial effects on preeclampsia, heart failure, myocardial infarction, stroke, resistant hypertension, secondary lymphedema and pulmonary arterial hypertension in a variety of animal models (Li et al. (2013) J Clin Invest 123: 2408-2420; Fritz-Six et al. (2008) J Clin Invest 118:40-50; Dackor et al. (2006) Mol Cell Biol 26:2511-2518; Caron and Smithies (2001) PNAS 98:615-619; Yoshizawa et al. (2013) Hypertension 61:341-351; Koyama et al. (2015) J Atheroscler Thromb 22:647-653; Shindo et al. (2013) Curr Protein Pept Sci 14:347-357; Niu et al. (2004) Circulation 109: 1789-1794).

For use in the subject methods, long-acting adrenomedullin, intermedin or variants (Table 1) thereof may be used. Peptides of interest include fragments of at least about 12 contiguous amino acids, more usually at least about 20 contiguous amino acids, and may comprise 30, 35, 40 or more amino acids, up to the complete peptide, and may extend further to comprise other sequences present in the precursor protein. Deletions may extend from residue 1 through 10 of the peptide, and may further delete additionally amino acids at residues 10-15 or more. Smaller deletions, of from 1 to 5 amino acids, may be deleted in the N-terminus or the middle of the sequence. Peptides of interest for therapeutic purposes may include all or substantially all of the provided peptides, or may comprise fragments thereof that retain the biological activity of adrenomedullin or intermedin.

The sequence of the polypeptide may be altered in various ways known in the art to generate targeted changes in sequence. The polypeptide will usually be substantially similar to the sequences provided herein, i.e. will have greater than 60%, greater than 70%, greater than 80%, greater than 90%, greater than 95% sequence identity with SEQ ID NO:2 or SEQ ID NOS: 3-34. The sequence changes may be substitutions, insertions or deletions. Scanning mutations that systematically introduce alanine, or other residues, may be used to determine key amino acids. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine).

Modifications of interest that do not alter primary sequence include chemical derivatization of polypeptides, e.g., acetylation, acylation, pegylation, or carboxylation. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes.

In specific embodiments, the long-acting CLR/RAMP receptor agonist is selected from a group consisting of adrenomedullin, intermedin, chimeric adrenomedullin/intermedin and modifications thereof as set forth in Table 1. The CLR/RAMP receptor agonist, or modifications thereof, is preferably a mammalian peptide, specifically, a mouse, rat, guinea pig, rabbit, dog, cat, horse, cow, pig, or primate peptide, or derivative thereof. Preferably, the peptide is a human peptide, or derivative thereof.

Modification of a long-acting CLR/RAMP receptor agonist as used in this invention comprises a change to the amino acid sequence of the compound at at least one position in the amino acid sequence, including amino acid insertions, deletions, and substitutions. Preferably, a modified long-acting CLR/RAMP receptor agonist binds to the CLR/RAMP receptors in a similar way as the unmodified peptide and thus displays similar or superior physiological activity.

In yet other embodiments, the long-acting CLR/RAMP receptor agonist comprises an optical isomer, enantiomer, diastereomer, tautomer, cis-trans isomer, racemate, prod rug or pharmaceutically acceptable salt of adrenomedullin, intermedin, chimeric adrenomedullin/intermedin, or their modifications. In a particular embodiment of the invention, the compound comprises a CLR/RAMP receptor agonist of an amino acid sequence as set forth in SEQ ID NO:2 or in SEQ ID NOS:3-34 containing a $CONH_2$ at its carboxy terminus and an N-terminal acylation of the amino acid sequence. Furthermore, compounds of the present invention refer to chemical or peptidic moieties that bind to or complex with CLR/RAMP receptors, such as adrenomedullin or mimetic adrenomedullin polypeptides. Preferred compounds are peptides that have an increased stability in vivo.

Embodiments of long-acting CLR/RAMP receptor agonists, which are amidated at the C-termini, are provided in Tables 1. The modified peptides optionally contain an acylation modification. Optionally, the number of acylation can be more than one, with one reactive group being preferable.

Drug compounds of the present invention also include a mixture of stereoisomers, or each pure or substantially pure isomer. For example, the present compound may optionally have one or more asymmetric centers at a carbon atom containing any one substituent. Therefore, the compound may exist in the form of enantiomer or diastereomer, or a mixture thereof. When the present compound contains a double bond, the present compound may exist in the form of geometric isomerism (cis-compound, trans-compound), and when the present compound contains an unsaturated bond such as carbonyl, then the present compound may exist in the form of a tautomer, and the present compound also includes these isomers or a mixture thereof. The starting compound in the form of a racemic mixture, enantiomer or diastereomer may be used in the processes for preparing the present compound. When the present compound is obtained in the form of a diastereomer or enantiomer, they can be separated by a conventional method such as chromatography or fractional crystallization. In addition, the present compound includes an intramolecular salt, hydrate, solvate or polymorphism thereof.

Also included in the subject invention are polypeptides that have been modified using ordinary molecular biological techniques and synthetic chemistry so as to improve their resistance to proteolytic degradation or to optimize solubility properties or to render them more suitable as a therapeutic agent. For examples, the backbone of the peptide may be cyclized by adding cyclic disulfide bridge or lactam bridge to enhance stability (see Friedler et al. (2000) *J. Biol. Chem.* 275:23783-23789). Analogs of such polypeptides include those containing residues other than naturally occurring L-amino acids, e.g. D-amino acids or non-naturally occurring synthetic amino acids.

The subject peptides may be prepared by in vitro synthesis, using conventional methods as known in the art. Various commercial synthetic apparatuses are available, for example, automated synthesizers by Applied Biosystems, Inc., Foster City, Calif., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99% by weight, in relation to contaminants related to the method of preparation of the product and its purification. Usually, the percentages will be based upon total protein.

Methods of Use

The long-acting CLR/RAMP receptor agonists are useful in reducing hypertension and improve vascular integrity, particularly hypertension associated with pregnancy, hypertensive crisis, resistant hypertension, or pulmonary arterial hypertension as well as endothelial dysfunction-associated diseases, including stroke, angina, cardioarterial diseases, myocardial infarction, renal failure, secondary lymphedema, and diabetic ulcers. The treatment reduces hypertension, e.g. systolic blood pressure, or mean arterial pressure, by at least about 5%, at least about 10%, at least about 15%, at least about 20% or more, without increasing heart rate. The treatment may decrease heart rate, i.e. tachycardia, by at least about 5%, at least about 10%, at least about 15%, at least about 20% or more In methods of use, an effective dose of a long-acting CLR/RAMP receptor agonist of the invention is administered alone or in a cocktail of peptides, or combined with additional active agents for the treatment hypertension, endothelial dysfunction, organ toxicity, and ischemic injury, including without limitation hypertension associated with hypertensive crisis, or pregnancy, such as pre-eclampsia. The effective dose in a rat model as shown herein, is appropriately converted to a human equivalent dose.

The effective daily dose for a human patient may be from about 10 µg/kg weight, 25 µg/kg weight, 50 µg/kg weight, 100 µg/kg weight, 250 µg/kg weight, 500 µg/kg weight, 750 µg/kg weight, 1 mg/kg weight, 5 mg/kg weight, 10 mg/kg weight, 25 mg/kg weight, 50 mg/kg weight, 75 mg/kg weight, 100 mg/kg weight, 250 mg/kg weight, 500 mg/kg weight, 750 mg/kg weight, 1 mg/kg weight and the like. The daily dose dosage may be fractionated into smaller doses administered multiple times as needed, e.g. every 30 minutes, every hour, every 2 hours, every 4 hours, every 6 hours, every 8 hours, every 12 hours, every 18 hours, daily, every 2 days, every 3 days, weekly, and the like. The dosage may also be administered as a continuous infusion, e.g. at a dose of from about 0.5 µg/kg/hr; from about 1 µg/kg/hr; from about 2 µg/kg/hr; from about 4 µg/kg/hr; from about 10 µg/kg/hr; from about 15 µg/kg/hr; from about 20 µg/kg/hr; from about 25 µg/kg/hr; from about 30 µg/kg/hr; from about 35 µg/kg/hr; from about 40 µg/kg/hr; from about 50 µg/kg/hr or more.

The effective dose may be maintained for a period of time sufficient to treat the hypertension and endothelial dysfunction, including stabilizing blood pressure and reducing ischemic injury in hypertensive crisis or pregnancy. Treatment may be for 1, 2, 3, 4, 5, 6, 7, 8, 9, 10, 11, 12, 13, 14 or more day, e.g. 1 week, 2 weeks, 3 weeks, 4 weeks or more. Treatment may be continuous, or intermittent, e.g. every other day, every third day, weekly, etc.

The peptides of the invention find use in reducing hypertension associated with hypertensive crisis, resistant hypertension, preeclampsia, or eclampsia, and may be administered for a period of time sufficient to stabilize the subject and allow for safe delivery of the pregnancy.

Preeclampsia is new-onset hypertension and proteinuria after 20 wk gestation. Eclampsia is unexplained generalized seizures in patients with preeclampsia. Diagnosis is clinical and by urine protein measurement. Conventional treatment is usually with IV Mg sulfate and delivery at term. Preeclampsia affects 3 to 7% of pregnant women. Preeclampsia and eclampsia develop after 20 wk gestation; up to 25% of cases develop postpartum, most often within the first 4 days but sometimes up to 6 wk postpartum. Untreated preeclampsia usually smolders for a variable time, then suddenly progresses to eclampsia, which occurs in 1/200 patients with preeclampsia. Untreated eclampsia is usually fatal.

Preeclampsia may be asymptomatic or may cause edema or excessive weight gain. Nondependent edema, such as facial or hand swelling (the patient's ring may no longer fit her finger), is more specific than dependent edema. Reflex reactivity may be increased, indicating neuromuscular irritability, which can progress to seizures (eclampsia). Petechiae may develop, as may other signs of coagulopathy.

Diagnosis is of new-onset hypertension (BP>140/90 mm Hg) plus new unexplained proteinuria>300 mg/24 h after 20 wk. Diagnosis is suggested by symptoms or presence of hypertension, defined as systolic BP>140 mm Hg, diastolic BP>90 mm Hg, or both. Except in emergencies, hypertension should be documented in >2 measurements taken at least 4 h apart. Urine protein excretion is measured in a 24-h collection. Proteinuria is defined as >300 mg/24 h. Alternatively, proteinuria is diagnosed based on a protein:creatinine ratio 0.3 or a dipstick reading of 1+ (used only if other quantitative methods are not available). Absence of proteinuria on less accurate tests (eg, urine dipstick testing, routine urinalysis) does not rule out preeclampsia.

In the absence of proteinuria, preeclampsia is also diagnosed if pregnant women have new-onset hypertension plus new onset of any of the following: Thrombocytopenia (platelets<100,000/µL); Renal insufficiency (serum creatinine >1.1 mg/dL or doubling of serum creatinine in women without renal disease), Impaired liver function (aminotransferases >2 times normal), Pulmonary edema, Cerebral or visual symptoms.

Hypertension is a disease which, if untreated, strongly predisposes to atherosclerotic cardiovascular disease. It is estimated that as many as 1 in 4 adult Americans have hypertension. Hypertension is approximately twice as common in persons with diabetes as in those without. The prevalence of hypertension increases with age.

Resistant hypertension is defined as persistent elevation of blood pressure above goal despite concurrent use of 3 antihypertensive agents, each of unique class with a diuretic included among the treatment regimen, and with all drugs at target dose. The prevalence of resistant hypertension is correlated with the number of coronary artery disease (CAD) risk factors including, cardiovascular-related comorbidities (e.g., heart failure and left-ventricular hypertrophy), diabetes, stroke, percutaneous coronary intervention, peripheral vascular disease, renal insufficiency, age, and BMI. The situation could be related to the fact that most of the existing antihypertensive drugs mainly target the (1) renin-angiotensin-aldosterone axis, (2) the sympathetic nervous activities, and (3) the endothelin signaling pathway, and act by blocking these signaling pathways. There is a lack of therapeutics that can actively reduce endothelial dysfunction and improve hemodynamics in patients with resistant hypertension.

Hypertension should not be diagnosed on the basis of a single measurement. Initial elevated readings should be confirmed on at least two subsequent visits over one week or more with average diastolic blood pressure of 90 mmHg or greater or systolic blood pressure of 140 mmHg or greater required for diagnosis of hypertension. Special care is warranted in diagnosing hypertension in persons with diabetes because of greater variability of blood pressure and a much greater likelihood of isolated systolic hypertension. A goal blood pressure of less than 130/85 mmHg is recommended for these patients.

In addition to dietary changes, pharmacological treatment may be required to control high blood pressure during pregnancy or when the subject develop resistant hypertension or hypertensive crisis. The subject peptides may be administered to reduce arterial blood pressure. In addition, a secondary effect of reducing hypertension is reduction of edema and inflammatory exudate volume.

Pharmaceutical compositions containing peptides of the invention are useful as cardioprotective agents and can be co-administered to mitigate the toxicity of cardiotoxic agents. Such agents include anthracycline based chemotherapy, comprising the administration of therapeutics that comprise the anthracycline class of antibiotic compounds. Anthracyclines are used to treat a wide range of cancers, including leukemias, lymphomas, and breast, uterine, ovarian and lung cancers. Examples of anthracyclines include daunorubicin, doxorubicin, epirubicin, idarubicin, valrubicin and mitoxantrone. An example of an anthracycline-based therapy would be one comprising cyclophosphamide, vincristine, doxorubicin and prednisone (CHOP).

Long-acting ADM analogs of the invention can be administered in combination with an anthracycline agent. In combination with", "combination therapy" and "combination products" refer, in certain embodiments, to the concurrent administration to a patient of a peptide of the invention and an anthracycline. When administered in combination, each component can be administered at the same time or sequentially in any order at different points in time. Thus, each component can be administered separately but sufficiently closely in time so as to provide the desired therapeutic effect. Alternatively a co-formulation can include an effective dose of each of the active agents in a single formulation.

"Concomitant administration" of two active agents as set forth in the present invention means administration with the two agents such that they will have a therapeutic effect. Such concomitant administration may involve concurrent (i.e. at the same time), prior, or subsequent administration of one agents with respect to the administration of the other agent. A person of ordinary skill in the art would have no difficulty determining the appropriate timing, sequence and dosages of administration for particular drugs and compositions of the present invention.

The effective dose for a human patient may be from about 1 nM/kg weight, 5 nM/kg weight, 10 nM/kg weight, 15 nM/kg weight, 20 nM/kg weight, 25 nM/kg weight, 50 nM/kg weight, 100 nM/kg weight, 250 nM/kg weight, 500 nM/kg weight and the like. The dose may be fractionated into smaller doses administered multiple times as needed, e.g. every 30 minutes, every hour, every 2 hours, every 4 hours, every 6 hours, every 8 hours, every 12 hours, every 18 hours, daily, every 2 days, every 3 days, weekly, and the like. The dosage may also be administered as a continuous infusion, e.g. in combination with the anthracycline.

The effective dose may be maintained for a period of time sufficient to mitigate cardiotoxicity. Treatment may be for 1, 2, 3, 4, 5, 6, 7, 8, 9, 10, 11, 12, 13, 14 or more day, e.g. 1 week, 2 weeks, 3 weeks, 4 weeks or more. Treatment may be continuous, or intermittent, e.g. every other day, every third day, weekly, etc.

Efficacy may be monitored by measuring indicia of cardiotoxicity, where the treatment provides for at least about a 10% improvement, at least about 20% improvement, at least about 30% improvement, at least about 40% improvement, at least about 50% improvement, or more. One biomarker exemplified herein is circulating levels of aspartate amino transferase.

Anthracycline-related cardiotoxicity is from a cumulative dose of the agent and usually begins as asymptomatic failures in the pumping of the heart that can progress to heart failure. It can present as abnormalities on electrocardiograms, irregular heartbeat, pericarditis-myocarditis syndrome (inflammation of the heart muscle or pericardium), or an increase in a brain natriuretic peptide (BNP) that is a marker of increased cardiac filling pressures. Nuclear imaging for cardiotoxicity checks cardiac function prior to and during treatment to determine if dose adjustments need to be made or other alternative treatment options explored. A common nuclear medicine heart test is the radionuclide angiogram (RNA). This scan measures the amount of blood ejected from the ventricle with each heart beat (ejection fraction). For example, if the left ventricle ejects 60% of its blood volume with each beat, the LVEF is 0.6 (normal is 0.5 or greater).

Other biomarkers for assessing cardiotoxicity include, without limitation, measurement of serum creatinine kinase-MB (CKMB; cardiac troponin (cTn) including high-sensitivity cardiac troponin (cTn); C-reactive protein (CRP); secreted miRNAs for example miR-126-3p, miR-30c and miR-26a in addition to miR-1, let-7 and miR-133; glycogen phosphorylase BB; soluble $CD_{40}$ ligand ($sCD_{40}L$); increase in the level of choline; $ST_2$; Endothelin-1 ($ET_1$) and C-terminal of pro-endothelin-1 ($CTproET_1$); heart-type FABP (HFABP) is a sensitive marker of myocyte damage; and the like.

Pharmaceutical Compositions

Some embodiments include pharmaceutical compositions comprising, as an active ingredient, a long-acting CLR/RAMP receptor agonist or a long-acting ADM analog (Table 1; including without limitation D-amino acids or peptidomimetics) disclosed herein in association with a pharmaceutical carrier or diluent. These pharmaceutical compositions can be administered by any means, as known to those of skill in the art, and include, without limitation, oral, pulmonary, parenteral (intramuscular, intraperitoneal, intravenous, or subcutaneous injection), inhalational (via a fine powder formulation, or aerosol), transdermal, intranasal or sublingual routes of administration and can be formulated in dosage forms appropriate for each route of administration. The compounds can also be administered in sustained or controlled release dosage forms, including without limitation, depot injections, osmotic pumps, transdermal (including electrotransport) patches, and the like, for prolonged and/or timed, pulsed administration at a predetermined rate.

The pharmaceutical compositions of the present embodiments may be manufactured in a manner that is itself known, e.g., by means of conventional mixing, dissolving, granulating, dragee-making, levigating, emulsifying, encapsulating, entrapping or tabletting processes. Pharmaceutical compositions for use in accordance with the present embodiments thus may be formulated in conventional manner using one or more physiologically acceptable carriers comprising excipients and auxiliaries which facilitate processing of the active compounds into preparations which can be used pharmaceutically. Any of the well-known techniques, carriers, and excipients may be used as suitable and as understood in the art.

Suitable excipients for use in the compositions include starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol. Whether a particular excipient is suitable for incorporation into a pharmaceutical composition depends on a variety of factors well known in the art including, but not limited to, the route of administration and the specific active ingredients in the composition. In certain embodiments of the invention, a composition is an anhydrous composition. Anhydrous compositions can be prepared using anhydrous or low moisture containing ingredients and low moisture or low humidity conditions. Compositions comprising modified peptides having a primary or secondary amine are preferably anhydrous if substantial contact with moisture and/or humidity during manufacturing, packaging, and/or storage is expected. Preferably, the compositions are also formulated to provide increased chemical stability of the compound during storage and transportation. The formulations may be lyophilized or liquid formulations.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For administration by inhalation, the instant compounds for use according to the present embodiments are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch. As an example, preparations for administration by inhalation may be prepared according to the teaching of Quay, et al., U.S. Pat. No. 7,812,120 B2.

Further disclosed herein are various pharmaceutical compositions well known in the pharmaceutical art for uses that include intraocular, intranasal, and intraauricular delivery. Suitable penetrants for these uses are generally known in the art. Pharmaceutical compositions for intraocular delivery include aqueous ophthalmic solutions of the active compounds in water-soluble form, such as eye drops, or in gellan gum; ophthalmic ointments; ophthalmic suspensions, such as microparticulates, drug-containing small polymeric particles that are suspended in a liquid carrier medium, lipid-soluble formulations; and ocular inserts. All of the above-mentioned references are incorporated herein by reference in their entireties. Such suitable pharmaceutical formulations are most often and preferably formulated to be sterile, isotonic and buffered for stability and comfort. Pharmaceutical compositions for intranasal delivery may also include drops and sprays often prepared to simulate in, many respects nasal secretions to ensure maintenance of normal ciliary action, such compositions include, for example and without limitation, the nasal solutions disclosed by Azria, et al., in U.S. Pat. No. 5,733,569. Pharmaceutical formulations for intraauricular delivery include suspensions and ointments for topical application in the ear. Common solvents for such aural formulations include glycerin and water.

In addition to the formulations described previously, the instant compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Non-limiting examples of methods of administration include, among others, (a) administration though non-oral pathways such as intraocular, intranasal or intraauricular, which administration includes administration as an aqueous suspension, an oily preparation or the like or as a drip, spray, salve, ointment or the like; (b) administration via injection, subcutaneously, intraperitoneally, intravenously, intramuscularly, intradermally, intraorbitally or the like, including infusion pump delivery; (c) administration locally such as by injection directly intracranially, e.g., by depot implantation; as well as (e) administration topically; as deemed appropriate by those of skill in the art for bringing the peptide of the present embodiments into contact with living tissue.

The exact formulation, route of administration and dosage for the pharmaceutical compositions of the present embodiments can be chosen by the individual physician in view of the patient's condition. Typically, the dose range of the composition administered to the patient can be from about 0.000001 to 100 mg/kg of the patient's body weight. The dosage may be a single one or a series of two or more given in the course of one or more days, as is needed by the patient.

In instances where human dosages for compounds have been established for at least some condition, the present embodiments will use those same dosages, or dosages that are between about 0.1% and 500%, more preferably between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

In certain embodiments, the compounds or derivative are administered in combination with one or more other biologically active agents as part of a treatment regimen. In certain embodiments, the compounds or derivatives are administered prior to, concurrently with, or subsequent to the administration of the one or more other biologically active agents. In one embodiment, the one or more other biologically active agents are administered in the same pharmaceutical composition with a compound or derivative described herein.

In another embodiment, the compound or derivative can be administered with one or more other compound or composition for reducing risk or treating a cardiovascular disease. Compounds or compositions the reduce the risk or treat cardiovascular disease include, but are not limited to, anti-inflammatory agents, anti-thrombotic agents, anti-platelet agents, fibrinolytic agents, thrombolytics, lipid reducing agents, direct thrombin inhibitors, anti-Xa inhibitors, anti-IIa inhibitors, glycoprotein IIb/IIIs receptor inhibitors and direct thrombin inhibitors. Examples of agents that can be administered in combination with the compound or derivatives described herein include bivalirudin, hirudin, hirugen, Angiomax, agatroban, PPACK, thrombin aptamers, aspirin, GPIIb/IIIa inhibitors (e.g., Integrelin), P2Y12 inhibitors, thienopyridine, ticlopidine, and clopidogrel.

Although the exact dosage will be determined on a drug-by-drug basis, in most cases, some generalizations regarding the dosage can be made. The daily dosage regimen for an adult human patient may be, for example, an intravenous, subcutaneous, or intramuscular dose of each active ingredient at an exemplary range of between 0.001 mg and 100 mg, or an exemplary range of between 0.005 mg and 5 mg. In cases of administration of a pharmaceutically acceptable salt, dosages may be calculated as the free base. In some embodiments, the composition is administered 0.1 to 4 times per day or as a single acute dose, for example to ameliorate hypertension. Alternatively the compositions as described herein may be administered by continuous intravenous infusion, preferably at a dose of each active ingredient up to 1000 mg per day. As will be understood by those of skill in the art, in certain situations it may be necessary to administer the peptides disclosed herein in amounts that exceed, or even far exceed, the above-stated, exemplary dosage range in order to effectively and aggressively treat particularly aggressive diseases or infections. In some embodiments, the peptides will be administered for a period of continuous therapy, for example for a week or more, or for months or years.

In cases of local administration or selective uptake, the effective local concentration of the drug may not be related to plasma concentration. The amount of the instant composition administered may be dependent on the subject being treated, on the subject's weight, the severity of the affliction, and the manner of administration.

Compounds disclosed herein can be evaluated for efficacy and toxicity using known methods. The results of such studies are often predictive of efficacy in animals, such as mammals, or more specifically, humans. Alternatively, the efficacy of particular compounds in an animal model, such as mice, rats, rabbits, or monkeys, may be determined using known methods.

The compositions containing the compounds can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective dose".

The compositions described herein can also be microencapsulated by, for example, the method of Tice and Bibi (in: *Treatise on Controlled Drug Delivery*, ed. A. Kydonieus, Marcel Dekker, N.Y. 1992, pp. 315-339).

The agonist peptides and peptidomimetics described herein are effective in treating CLR/RAMP receptor-mediated conditions when administered at an exemplary dosage range of, for example, from about 0.01 µg to about 50 mg/kg of body weight per day. The specific dose employed is regulated by the particular condition being treated, the route of administration as well as by the judgment of the attending clinician depending upon factors such as the severity of the condition, the age and general condition of the patient, and the like. Such doses can be readily determined by those of skill in the art.

For parenteral administration, the peptides can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (for example, sodium chloride, mannitol) and chemical stability (for example, buffers and preservatives).

The compounds can be administered in a time release formulation, for example in a composition which includes a slow release polymer. Biodegradable, biocompatible polymers can be used, such as ethylene vinyl acetate, polyanhydrides, polyglycolic acid (PLG), collagen, polyorthoesters, polylactic acid (PLA) and poly(lactic-co-glycolic acid) (PLGA). Many methods for the preparation of such formulations are generally known to those skilled in the art.

Experimental

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLE 1

Modification of adrenomedullin, intermedin and chimeric adrenomedullin/intermedin (Table 1). Peptides were synthesized on an automated peptide synthesizer using standard solid-phase Fmoc peptide chemistry (Fields G B, Noble R L. Solid phase peptide synthesis utilizing 9-fluorenylmethoxycarbonyl amino acids. Int J Pept Protein Res 35: 161-214, 1990). The modified peptides was synthesized by incorporating lysine residue that has been conjugated to an Fmoc-protected [C16]palmitate fatty acid (Lys(PAL)) during the synthesis of peptides. Purity was determined by reversed-phase HPLC and subsequently characterized using electrospray ionisation mass spectrometry.

EXAMPLE 2

Figure 1B:
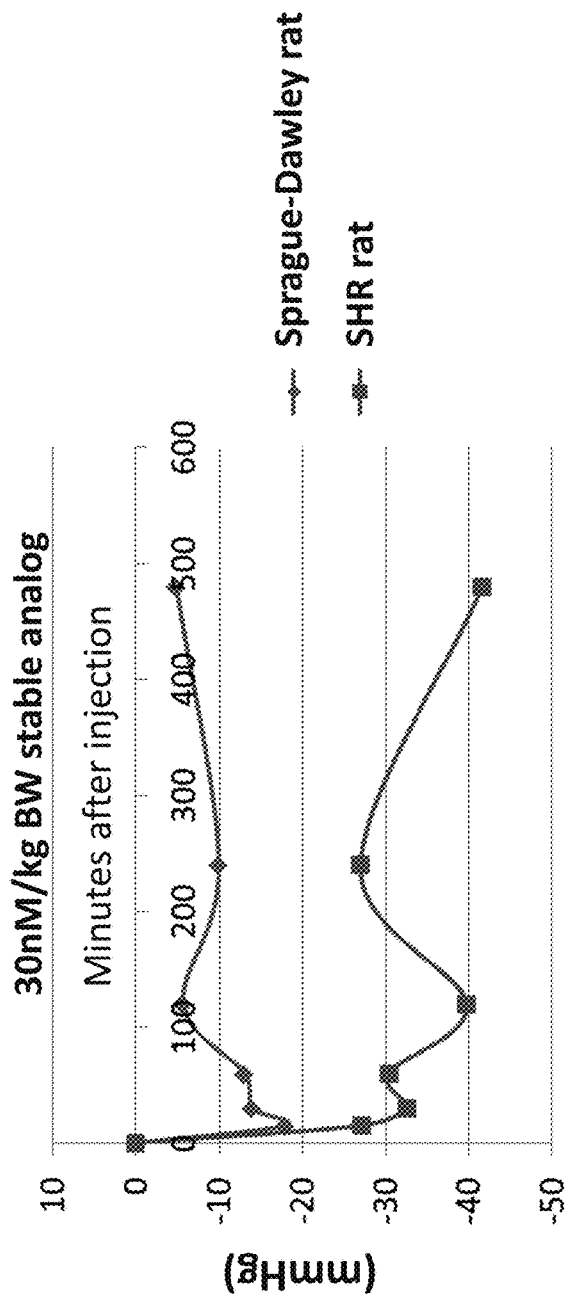

Effects of Long-Acting CLR/RAMP Receptor Agonist on Blood Pressure in Normal Sprague-Dawley Rats and Spontaneous Hypertenive (SHR) Rats To demonstrate that the long-acting CLR/RAMP receptor agonists have a long-lasting effects in vivo, we determined the effects of a long-acting ADM analog (SEQ ID NO:2; labeled as stable analog in all figures) on hemodynamics in instrumented pregnant rats. Bolus IP injection of the long-acting stable analog (100 nmoles/kg) led to a sustained reduction of blood pressure for 4 hr in normal pregnant Sprague Dawley rats, whereas the hypotensive effects of wild-type ADM disappeared within 2 hr (FIG. 1a). In addition, we compared the blood pressure-lowering effect of the long-acting stable analog in pregnant Sprague Dawley rats and pregnant spontaneous hypertensive rats (SHR). As shown in FIG. 1b, administration of a low dose of the long-acting stable analog (30 nmoles/kg) consistently reduced blood pressure for 2 hr in pregnant Sprague Dawley rats. In contrast, the hypotensive effects of the long-acting stable analog lasted over 8 hr in pregnant SHR rats (FIG. 1b), suggesting that the beneficial effects of long-acting CLR/RAMP receptor agonists could be particularly obvious under hypertensive conditions. Taken together, these data indicated that long-acting CLR/RAMP receptor agonists have a sustained effect on CLR/RAMP receptor signaling, endothelial function, vascular integrity, and hemodynamics in vivo. This characteristic not only allows less frequent dosing in clinical condition but also increases the therapeutic index of long-acting CLR/RAMP receptor agonists.

EXAMPLE 3

Effects of Long-Acting Stable Analog on Reduced Uterine Perfusion Pressure (RUPP)-Induced Preeclampsia in Pregnant Rats Materials and Methods To evaluate the effects of the long-acting stable analog for the treatment of preeclampsia, resistant hypertension, hypertensive crisis, vascular ischemic injury, and pregnancy hypertension, we tested the analog in a reduced uterine perfusion pressure (RUPP) preeclampsia rat model. The model was first described by Dr. Joey P. Granger et al. (2000, Hypertension 37:1191-1195). Briefly, pregnant rats weighing 200-250 g at 14 days of gestation were anesthetized with pentobarbital (40 mg/kg, i.p.). The lower abdomen area was shaved and the skin was swabbed with surgical scrub (iodine and alcohol). A 3-cm skin incision was made at the midline. After a midline incision, the lower abdominal aorta was isolated and a silver clip (0.203 mm) was placed around the aorta above the iliac bifurcation. Because compensatory blood flow to the placenta occurs via an adaptive increase in uterine blood flow during pregnancy, both right and left uterine arcades were clipped (silver clip, 0.100 mm). RUPP rats were divided into two groups, and an osmotic mini-pump (ALZET) loaded with saline or the long-acting analog was implanted in the upper abdomen. The mini-pumps delivered the solution at a rate of 1 ul/hr. Sham pregnant rats were used as normal controls.

The incision was closed with absorbable braided surgical suture. After awake, animals were given buprenorphine 0.1 mg/kg s.c. once a day for three days. These procedures reduced uterine blood flow in the gravid rat by >40%, and cause hypertension and intrauterine growth restriction in the fetus.

After 4 days of the treatments, all rats were anesthetized and catheterized for measurement of blood pressure and heart rate. Animals were anesthetized with pentobarbital, and a Mikro-tip catheter (1.0 F pressure catheter, Miller, Tex.) was placed into the right carotid artery. After insertion, the catheter was advanced into the aorta, and stopped at the appearance of arterial pressure curve. The Mikro-tip catheter was connected to a Powerlab system, and blood pressure and heart rate was recorded and saved in a computer. In addition, the blood flow velocity above and below the artery constriction site was determined by a Doppler method.

After the hemodynamic measurement was completed (taking about 0.5-1 hr), rats were euthanized. The fetuses, placenta tissues, and hearts were harvested and weighed individually.

Results

In a low-dose treatment study, each pregnant rat received 3.3 µg/kg/hr of the long-acting stable analog, or saline for four days. When compared to the sham controls, RUPP control rats have significantly increased mean arterial pressure (shame control, 102±3 mmHg (N=11) vs. RUPP controls, 114±3 mmHg (N=10); P=0.04, FIG. 2a). When the RUPP rats were treated with the low-dose long-acting stable analog (RUPP-stable analog group), the mean arterial pressure was reduced to 107±4 mmHg (N=9). However, the difference between the RUPP-control group and the RUPP-stable analog group was not statistically significant.

Figure 2B:
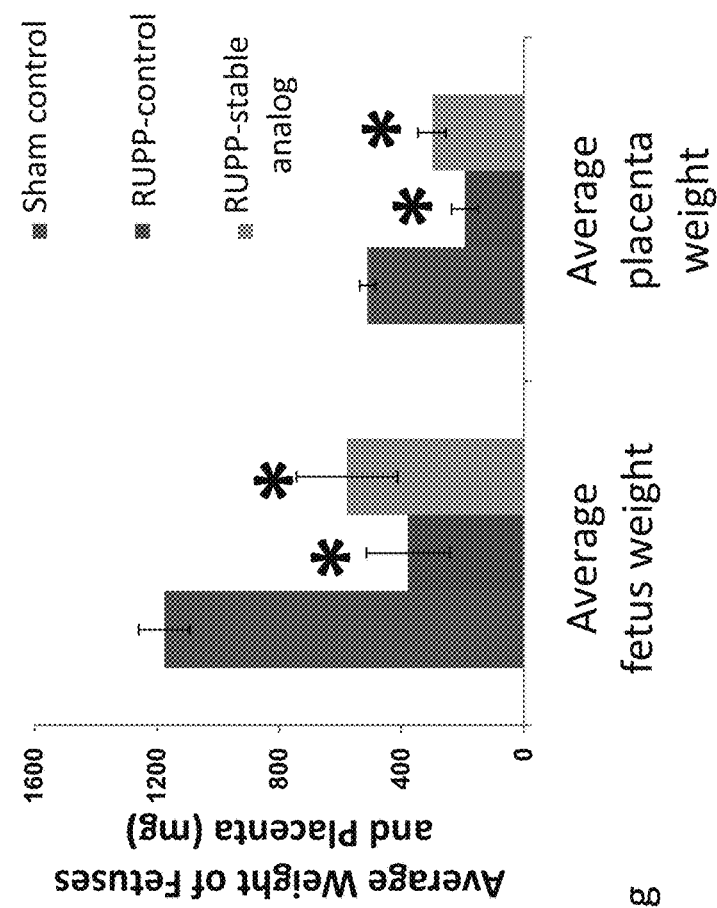
FIG. 2A-2B.
Figure 2A:
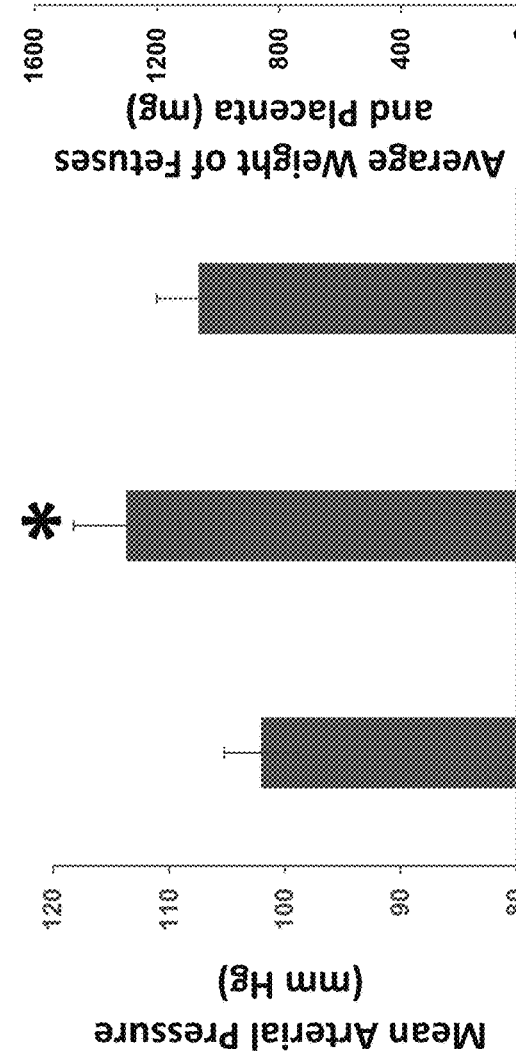

The average placenta weight of sham controls was 510±26 mg (N=11, FIG. 2b). The placenta weight was significantly reduced in both RUPP-control (193±43 mg, N=9) and the RUPP-stable analog (301±46 mg, N=9) groups. Although treatments with the long-acting analog appeared to increase the average placenta weight, the difference was only at the border of significance (P=0.10).

Likewise, the average fetus weight was significantly reduced by RUPP treatment (sham control, 1177±84 mg (N=11) vs. RUPP-control, 378±136 mg (N=9); FIG. 2b). The fetus weight was significantly reduced in the RUPP-stable analog (577±166 mg, N=9) group as well. No difference in the fetus weight between the RUPP-control and the RUPP-stable analog groups was observed.

In a high-dosage treatment study, each pregnant rat received 10 µg/kg/hr of the long-acting stable analog, or saline for four days. The mean arterial pressure of sham animals was 97±1 mmHg (FIG. 3a), and the RUPP treatment led to significant increases of mean arterial pressure (RUPP-control, 118±2 mmHg). The RUPP-induced hypertension in pregnant rats was significantly reduced by the long-acting analog treatment (RUPP-ADE, 93±5 mmHg, P=0.0002).

The RUPP treatment also led to a significant increase of heart rate in pregnant rats (sham control, 399±8 beats/min vs. RUPP-control, 438±13 beats/min; P=0.01; FIG. 3b). Similar to the effects on mean arterial pressure, the long-acting stable analog treatment significantly reduced the RUPP-induced tachycardia (RUPP-ADE, 379±8 beats/min, P=0.001).

The average placenta weight of sham controls was 470±24 mg (FIG. 3c), and was significantly reduced in the RUPP-control rats (125±18 mg). Consistent with the protective effects on RUPP-induced hypertension and tachycardia, the long-acting stable analog treatment significantly increased the average placenta weight in RUPP rats (RUPP-ADE, 253±36 mg; P=0.007).

Likewise, the RUPP treatment reduced the average fetus weight from 1028±36 mg in sham control rats to 192±44 mg in the RUPP-control rats (FIG. 3d). When the RUPP rats were treated with the long-acting stable analog, the average fetus weight was significantly increased (RUPP-ADE, 483±92 mg, P=0.01).

We also determined the body weight of pregnant rats during the four-day experimental period, and recorded changes in body weight. As shown in FIG. 3e, the sham controls gained an average of 40±4 grams, whereas the RUPP-control rats lost an average of 25±8 grams. By contrast, the RUPP-ADE rats lost an average of only 3±3 grams, which is significantly less than that of RUPP-control rats (P=0.03).

In addition, we determined the heart weights at the end of experiments. The average heart weight of sham controls was 2.95±0.07 mg per gram body weight (FIG. 3f). The RUPP treatment led to cardiac hypertrophy, and the average heart weight of RUPP-control animals was significantly increased (RUPP-control, 3.59±0.15 mg per gram body weight, P=0.002; FIG. 3f), and the RUPP-induced cardiac hypertrophy was significantly reduced by long-acting stable analog treatment (RUPP-ADE, 3.16±0.06 mg per gram body weight, P=0.02; FIG. 3f).

As a control, we also measured the blood flow velocity above and below the artery constriction site in order to monitor the degree of uterine perfusion reduction among animals. As expected, no difference in blood flow velocity above the constriction sites was observed among the three treatment groups (FIG. 3g). By contrast, the blood flow velocity below the constriction sites was reduced by more than 50% in both RUPP-control and RUPP-ADE animals. Importantly, the blood flow velocity below the constriction sites was almost identical in the RUPP-control and RUPP-ADE groups, indicating that the observed physiological changes between RUPP-control and RUPP-ADE groups were not a result of differences in surgical treatments.

EXAMPLE 4

Effects of Long-Acting Stable Analog on Doxorubicin-Induced Heart Failure in Adult Mice Materials and Methods To evaluate the effects of the long-acting stable analog on heart failure, we treated 8-week-old C57/B6 mice with doxorubicin (10 mg/kg body weight) to induce cardiomyopathy. After the injection of doxorubicin, the animals were injected with wild-type ADM or the long-acting stable analog twice daily. After five days of treatment, the animals were sacrificed, and hearts were collected for weight determination individually. In addition, we collected blood samples for the determination of aspartate aminotransferase activity. Sham adult mice at the same ages were used as normal controls.

Results

Figure 4A:
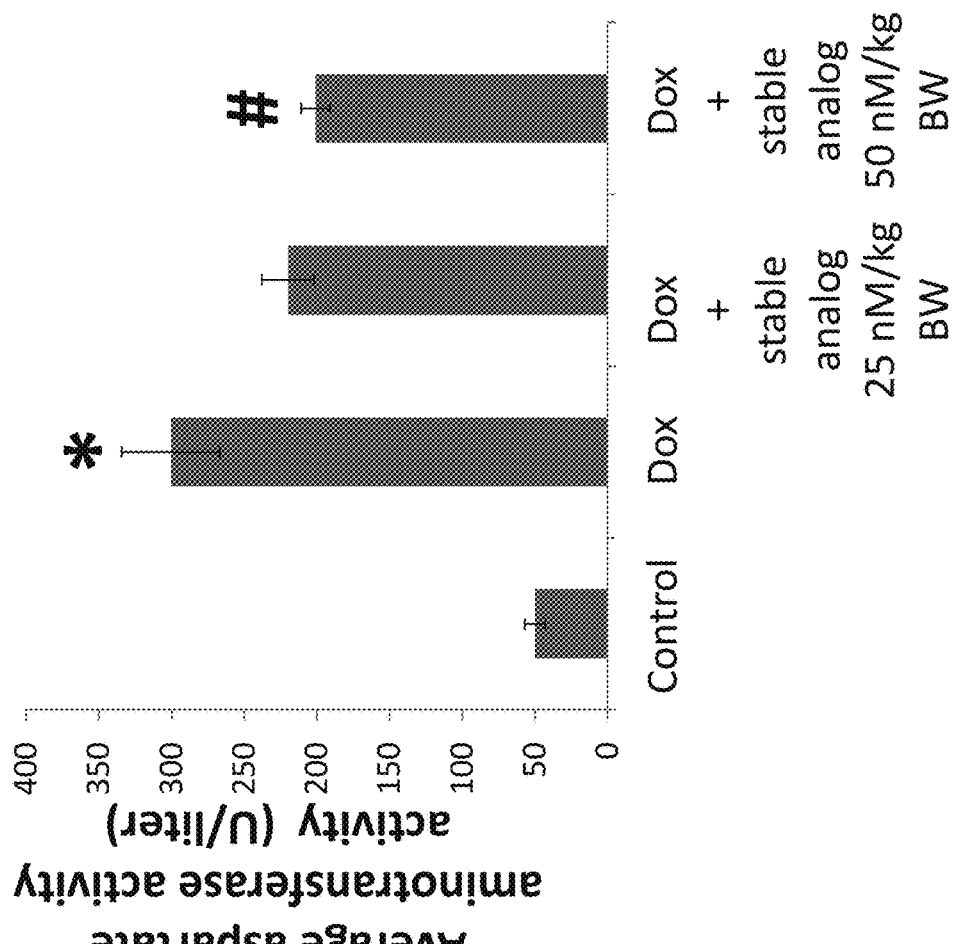
FIG. 4A-4B. Treatment of a long-acting stable analog significantly reduced the doxorubicin-induced cardiomyopathy and liver toxicity. The average heart weight of adult mice was significantly reduced by doxorubicin (Dox) treatment when compared to control mice (Control) FIG. 4A, whereas the doxorubicin treatment elevated blood aspartate aminotransferase level significantly FIG. 4B. The doxorubicin-induced cardiomyopathy and liver toxicity was significantly reduced by co-treatment with the long-acting stable analog (Dox+stable analog group). On the other hand, the wild-type ADM has minimal effects on doxorubicin-induced cardiomyopathy (Dox+ADM group). Significant differences between the sham control and Dox groups are indicated by asterisks (P<0.05). Significant differences between the Dox and Dox+stable analog groups are indicated by # symbols (P<0.05).

At the sixth day of the experiment, the average heart weight of sham controls was 11.4±0.6 mg. When the animals were treated with doxorubicin, the average heart weight was reduced to 9.3±0.4 mg (Control group vs. Dox group, P=0.01, FIG. 4a). On the other hand, when the animals were co-treated with the long-acting stable analog (i.e., stable analog), the doxorubicin-induced loss of heart weight was significantly reduced (Dox+stable analog group, 11.0±0.6 mg; P=0.03). The loss of heart weight in animals receiving doxorubicin plus wild-type ADM was also reduced; however, the reduction was not statistically significant (Dox group vs. Dox+ADM group, P=0.07).

Figure 4B:
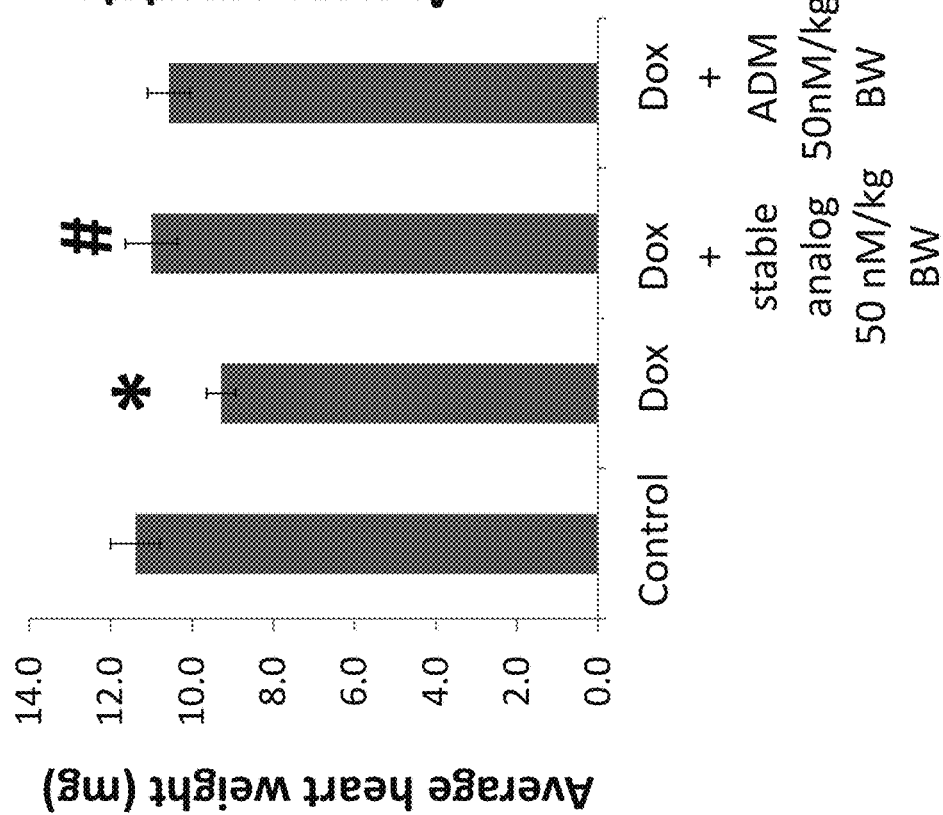

In a separate series of study, we evaluated the effects of stable analog on blood aspartate aminotransferase levels (FIG. 4b). Whereas the doxorubicin treatment significantly elevated aspartate aminotransferase level when compared to control mice (control mice, 50±7.2 U/liter vs. Dox mice, 300.7±33.6 U/liter; P=0.00009), co-treatment with a high-dose of long-acting stable analog significantly reduced the doxorubicin-induced liver toxicity in mice (Dox+stable analog, 50 nM/Kg body weight (BW); 200.1±10.0 U/liter; P=0.03), whereas treatment with a low-dose of long-acting stable analog (25 nM/Kg BW) has no statistically significant effect. These data suggested that the long-acting stable analog has protective effects on multiple organs.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. Moreover, due to biological functional equivalency considerations, changes can be made in protein structure without affecting the biological action in kind or amount. All such modifications are intended to be included within the scope of the appended claims.

What is claimed is:

1. A method for reducing cardiotoxicity, the method comprising: administering a long-acting CLR/RAMP receptor agonist peptide selected from the group consisting of SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22; SEQ ID NO:23; SEQ ID NO:25; SEQ ID NO:26; SEQ ID NO:28; SEQ ID NO:31; SEQ ID NO:32; SEQ ID NO:34, to a subject in need thereof at a dose of at least about 0.5 g/kg weight for a period of time sufficient to reduce cardiotoxicity.

2. The method of claim 1, wherein the cardiotoxicity is associated with administering of an anthracycline or a tyrosine kinase receptor antagonist.

3. The method of claim 2, wherein the anthracycline is doxorubicin.

4. The method of claim 3, wherein the CLR/RAMP receptor agonist is co-administered with the doxorubicin.

5. A method for reducing cardiotoxicity, the method comprising: administering subcutaneously a long-acting CLR/RAMP receptor agonist consisting of the amino acid sequence set forth in SEQ ID NO:18 to a subject in need thereof at a dose of at least about 0.5 g/kg weight for a period of time sufficient to reduce cardiotoxicity.

6. The method of claim 5, wherein the cardiotoxicity is associated with administering of an anthracycline or a tyrosine kinase receptor antagonist.

7. The method of claim 6, wherein the anthracycline is doxorubicin.

8. The method of claim 7, wherein the CLR/RAMP receptor agonist is co-administered with the doxorubicin.

* * * * *

SEQUENCE LISTING

```
<160> NUMBER OF SEQ ID NOS: 34

<210> SEQ ID NO 1
<211> LENGTH: 185
<212> TYPE: PRT
<213> ORGANISM: Homo sapiens

<400> SEQUENCE: 1

Met Lys Leu Val Ser Val Ala Leu Met Tyr Leu Gly Ser Leu Ala Phe
1               5                   10                  15

Leu Gly Ala Asp Thr Ala Arg Leu Asp Val Ala Ser Glu Phe Arg Lys
            20                  25                  30

Lys Trp Asn Lys Trp Ala Leu Ser Arg Gly Lys Arg Glu Leu Arg Met
        35                  40                  45

Ser Ser Ser Tyr Pro Thr Gly Leu Ala Asp Val Lys Ala Gly Pro Ala
    50                  55                  60

Gln Thr Leu Ile Arg Pro Gln Asp Met Lys Gly Ala Ser Arg Ser Pro
65                  70                  75                  80

Glu Asp Ser Ser Pro Asp Ala Ala Arg Ile Arg Val Lys Arg Tyr Arg
                85                  90                  95

Gln Ser Met Asn Asn Phe Gln Gly Leu Arg Ser Phe Gly Cys Arg Phe
            100                 105                 110

Gly Thr Cys Thr Val Gln Lys Leu Ala His Gln Ile Tyr Gln Phe Thr
        115                 120                 125

Asp Lys Asp Lys Asp Asn Val Ala Pro Arg Ser Lys Ile Ser Pro Gln
    130                 135                 140

Gly Tyr Gly Arg Arg Arg Arg Ser Leu Pro Glu Ala Gly Pro Gly
145                 150                 155                 160

Arg Thr Leu Val Ser Ser Lys Pro Gln Ala His Gly Ala Pro Ala Pro
                165                 170                 175

Pro Ser Gly Ser Ala Pro His Phe Leu
            180                 185

<210> SEQ ID NO 2
<211> LENGTH: 39
<212> TYPE: PRT
<213> ORGANISM: Artificial Sequence
<220> FEATURE:
```

```
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (39)..(39)
<223> OTHER INFORMATION: AMIDATION

<400> SEQUENCE: 2

Lys Gly Cys Arg Phe Gly Thr Cys Thr Val Gln Lys Leu Ala His Gln
1               5                  10                  15

Ile Tyr Gln Phe Thr Asp Lys Asp Lys Asp Asn Val Ala Pro Arg Ser
            20                  25                  30

Lys Ile Ser Pro Gln Gly Tyr
        35

<210> SEQ ID NO 3
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue is modified with 11-amino-3,6,9-
      trioxaundecanoic acid
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (39)..(39)
<223> OTHER INFORMATION: AMIDATION

<400> SEQUENCE: 3

Lys Gly Cys Arg Phe Gly Thr Cys Thr Val Gln Lys Leu Ala His Gln
1               5                  10                  15

Ile Tyr Gln Phe Thr Asp Lys Asp Lys Asp Asn Ser Ala Pro Val Asp
            20                  25                  30

Pro Ser Ser Pro His Ser Tyr
        35

<210> SEQ ID NO 4
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue is modified with 11-amino-3,6,9-
      trioxaundecanoic acid
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (39)..(39)
<223> OTHER INFORMATION: AMIDATION

<400> SEQUENCE: 4
```

Lys Gly Cys Arg Phe Gly Thr Cys Thr Val Gln Lys Leu Ala His Gln
1               5                   10                  15

Ile Tyr Gln Phe Thr Pro Ala Gly Arg Gln Asp Ser Ala Pro Val Asp
            20                  25                  30

Pro Ser Ser Pro His Ser Tyr
        35

<210> SEQ ID NO 5
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (39)..(39)
<223> OTHER INFORMATION: AMIDATION

<400> SEQUENCE: 5

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Ser Ala Pro Val Asp
            20                  25                  30

Pro Ser Ser Pro His Ser Tyr
        35

<210> SEQ ID NO 6
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (39)..(39)
<223> OTHER INFORMATION: AMIDATION

<400> SEQUENCE: 6

Lys Gly Cys Arg Phe Gly Thr Cys Thr Val Gln Lys Leu Ala His Gln
1               5                   10                  15

Ile Tyr Gln Phe Thr Pro Ala Gly Arg Gln Asp Ser Ala Pro Val Asp
            20                  25                  30

Pro Ser Ser Pro His Ser Tyr
        35

<210> SEQ ID NO 7
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: LIPID
<222> LOCATION: (1)..(1)
<223> OTHER INFORMATION: PALMITATE

```
<220> FEATURE:
<221> NAME/KEY: MOD_RES
<222> LOCATION: (39)..(39)
<223> OTHER INFORMATION: AMIDATION

<400> SEQUENCE: 7

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Ser Ala Pro Val Asp
            20                  25                  30

Pro Ser Ser Pro His Ser Tyr
            35

<210> SEQ ID NO 8
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (39)..(39)
<223> OTHER INFORMATION: AMIDATION

<400> SEQUENCE: 8

Lys Gly Cys Arg Phe Gly Thr Cys Thr Val Gln Lys Leu Ala His Gln
1               5                   10                  15

Ile Tyr Gln Phe Thr Pro Ala Gly Arg Gln Asp Ser Ala Pro Val Asp
            20                  25                  30

Pro Ser Ser Pro His Ser Tyr
            35

<210> SEQ ID NO 9
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (39)..(39)
<223> OTHER INFORMATION: AMIDATION

<400> SEQUENCE: 9

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Val Asp
            20                  25                  30

Pro Ser Ser Pro His Ser Tyr
            35

<210> SEQ ID NO 10
<211> LENGTH: 39
<212> TYPE: PRT
<213> ORGANISM: Artificial sequence
```

```
<220> FEATURE:
<223> OTHER INFORMATION: Synthetic polypeptide

<400> SEQUENCE: 10

Lys Gly Cys Arg Phe Gly Thr Cys Thr Val Gln Lys Leu Ala His Gln
1               5                   10                  15

Ile Tyr Gln Phe Thr Asp Lys Asp Lys Gln Asp Ser Ala Pro Val Asp
            20                  25                  30

Pro Ser Ser Pro His Ser Tyr
        35

<210> SEQ ID NO 11
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (39)..(39)
<223> OTHER INFORMATION: AMIDATION

<400> SEQUENCE: 11

Lys Gly Cys Arg Phe Gly Thr Cys Thr Val Gln Lys Leu Ala His Gln
1               5                   10                  15

Ile Tyr Gln Phe Thr Asp Lys Gly Arg Gln Asp Ser Ala Pro Val Asp
            20                  25                  30

Pro Ser Ser Pro His Ser Tyr
        35

<210> SEQ ID NO 12
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (39)..(39)
<223> OTHER INFORMATION: AMIDATION

<400> SEQUENCE: 12

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Ser Ala Pro Val Asp
            20                  25                  30

Pro Ser Ser Pro His Ser Tyr
        35

<210> SEQ ID NO 13
<211> LENGTH: 46
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
```

```
<220> FEATURE:
<221> NAME/KEY: MOD_RES
<222> LOCATION: (46)..(46)
<223> OTHER INFORMATION: AMIDATION

<400> SEQUENCE: 13

Lys Thr Lys Lys Thr Leu Arg Thr Gly Cys Arg Phe Gly Thr Cys Thr
1               5                   10                  15

Val Gln Lys Leu Ala His Gln Ile Tyr Gln Phe Thr Asp Lys Asp Lys
            20                  25                  30

Asp Asn Ser Ala Pro Val Asp Pro Ser Ser Pro His Ser Tyr
            35                  40                  45

<210> SEQ ID NO 14
<211> LENGTH: 45
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: LIPID
<222> LOCATION: (2)..(2)
<223> OTHER INFORMATION: PALMITATE
<220> FEATURE:
<221> NAME/KEY: MOD_RES
<222> LOCATION: (45)..(45)
<223> OTHER INFORMATION: AMIDATION

<400> SEQUENCE: 14

Thr Lys Lys Thr Leu Arg Thr Gly Cys Arg Phe Gly Thr Cys Thr Val
1               5                   10                  15

Gln Lys Leu Ala His Gln Ile Tyr Gln Phe Thr Asp Lys Asp Lys Asp
            20                  25                  30

Asn Ser Ala Pro Val Asp Pro Ser Ser Pro His Ser Tyr
            35                  40                  45

<210> SEQ ID NO 15
<211> LENGTH: 46
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (46)..(46)
<223> OTHER INFORMATION: AMIDATION

<400> SEQUENCE: 15

Lys Thr Lys Lys Thr Leu Arg Thr Gly Cys Arg Phe Gly Thr Cys Thr
1               5                   10                  15

Val Gln Lys Leu Ala His Gln Ile Tyr Gln Phe Thr Asp Lys Asp Lys
            20                  25                  30

Asp Asn Val Ala Pro Val Asp Pro Ser Ser Pro His Ser Tyr
            35                  40                  45

<210> SEQ ID NO 16
<211> LENGTH: 45
<212> TYPE: PRT
<213> ORGANISM: Artificial sequence
```

```
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: LIPID
<222> LOCATION: (2)..(2)
<223> OTHER INFORMATION: PALMITATE
<220> FEATURE:
<221> NAME/KEY: MOD_RES
<222> LOCATION: (45)..(45)
<223> OTHER INFORMATION: AMIDATION

<400> SEQUENCE: 16

Thr Lys Lys Thr Leu Arg Thr Gly Cys Arg Phe Gly Thr Cys Thr Val
1               5                   10                  15

Gln Lys Leu Ala His Gln Ile Tyr Gln Phe Thr Asp Lys Asp Lys Asp
            20                  25                  30

Asn Val Ala Pro Val Asp Pro Ser Ser Pro His Ser Tyr
        35                  40                  45

<210> SEQ ID NO 17
<211> LENGTH: 45
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue is modified with 11-amino-3,6,9-
      trioxaundecanoic acid
<220> FEATURE:
<221> NAME/KEY: LIPID
<222> LOCATION: (2)..(2)
<223> OTHER INFORMATION: PALMITATE
<220> FEATURE:
<221> NAME/KEY: MOD_RES
<222> LOCATION: (45)..(45)
<223> OTHER INFORMATION: AMIDATION

<400> SEQUENCE: 17

Thr Lys Lys Thr Leu Arg Thr Gly Cys Arg Phe Gly Thr Cys Thr Val
1               5                   10                  15

Gln Lys Leu Ala His Gln Ile Tyr Gln Phe Thr Asp Lys Asp Lys Asp
            20                  25                  30

Asn Val Ala Pro Val Asp Pro Ser Ser Pro His Ser Tyr
        35                  40                  45

<210> SEQ ID NO 18
<211> LENGTH: 38
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue is modified with 11-amino-3,6,9-
      trioxaundecanoic acid
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (38)..(38)
<223> OTHER INFORMATION: AMIDATION
```

-continued

<400> SEQUENCE: 18

Lys Cys Arg Phe Gly Thr Cys Thr Val Gln Lys Leu Ala His Gln Ile
1               5                   10                  15

Tyr Gln Phe Thr Asp Lys Asp Lys Asp Asn Ser Ala Pro Val Asp Pro
            20                  25                  30

Ser Ser Pro His Ser Tyr
        35

<210> SEQ ID NO 19
<211> LENGTH: 38
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (38)..(38)
<223> OTHER INFORMATION: AMIDATION

<400> SEQUENCE: 19

Lys Cys Arg Phe Gly Thr Cys Thr Val Gln Lys Leu Ala His Gln Ile
1               5                   10                  15

Tyr Gln Phe Thr Asp Lys Asp Lys Asp Asn Ser Ala Pro Val Asp Pro
            20                  25                  30

Ser Ser Pro His Ser Tyr
        35

<210> SEQ ID NO 20
<211> LENGTH: 38
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (38)..(38)
<223> OTHER INFORMATION: AMIDATION

<400> SEQUENCE: 20

Gly Cys Arg Phe Gly Thr Cys Thr Val Gln Lys Leu Ala His Gln Ile
1               5                   10                  15

Tyr Gln Phe Thr Asp Lys Asp Lys Asp Asn Ser Ala Pro Val Asp Pro
            20                  25                  30

Ser Ser Pro His Ser Tyr
        35

<210> SEQ ID NO 21
<211> LENGTH: 38
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue is modified with 11-amino-3,6,9-
      trioxaundecanoic acid
<220> FEATURE:
<221> NAME/KEY: LIPID

```
<222> LOCATION: (1)..(1)
<223> OTHER INFORMATION: PALMITATE
<220> FEATURE:
<221> NAME/KEY: MOD_RES
<222> LOCATION: (38)..(38)
<223> OTHER INFORMATION: AMIDATION

<400> SEQUENCE: 21

Lys Gly Cys Arg Phe Gly Thr Cys Thr Val Gln Lys Leu Ala His Gln
1               5                   10                  15

Ile Tyr Gln Phe Thr Asp Lys Asp Lys Asp Ser Ala Pro Val Asp Pro
            20                  25                  30

Ser Ser Pro His Ser Tyr
        35

<210> SEQ ID NO 22
<211> LENGTH: 37
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue is modified with 11-amino-3,6,9-
      trioxaundecanoic acid
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (37)..(37)
<223> OTHER INFORMATION: AMIDATION

<400> SEQUENCE: 22

Lys Gly Cys Arg Phe Gly Thr Cys Thr Val Gln Lys Leu Ala His Gln
1               5                   10                  15

Ile Tyr Gln Phe Thr Asp Lys Asp Lys Ser Ala Pro Val Asp Pro Ser
            20                  25                  30

Ser Pro His Ser Tyr
        35

<210> SEQ ID NO 23
<211> LENGTH: 36
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue is modified with 11-amino-3,6,9-
      trioxaundecanoic acid
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (36)..(36)
<223> OTHER INFORMATION: BLOCKED

<400> SEQUENCE: 23

Lys Gly Cys Arg Phe Gly Thr Cys Thr Val Gln Lys Leu Ala His Gln
1               5                   10                  15

Ile Tyr Gln Phe Thr Asp Lys Asp Ser Ala Pro Val Asp Pro Ser Ser
            20                  25                  30
```

```
Pro His Ser Tyr
        35

<210> SEQ ID NO 24
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue is modified with 11-amino-3,6,9-
      trioxaundecanoic acid
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (39)..(39)
<223> OTHER INFORMATION: AMIDATION

<400> SEQUENCE: 24

Lys Gly Cys Arg Phe Gly Thr Cys Thr Val Gln Lys Leu Ala His Gln
1               5                   10                  15

Ile Tyr Gln Phe Thr Pro Ala Gly Arg Gln Asp Ser Ala Pro Val Asp
            20                  25                  30

Pro Ser Ser Pro His Ser Tyr
        35

<210> SEQ ID NO 25
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue is modified with 11-amino-3,6,9-
      trioxaundecanoic acid
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (39)..(39)
<223> OTHER INFORMATION: AMIDATION

<400> SEQUENCE: 25

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Val Asp
            20                  25                  30

Pro Ser Ser Pro His Ser Tyr
        35

<210> SEQ ID NO 26
<211> LENGTH: 39
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue is modified with 11-amino-3,6,9-
      trioxaundecanoic acid
```

```
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (39)..(39)
<223> OTHER INFORMATION: AMIDATION

<400> SEQUENCE: 26

Lys Gly Cys Arg Phe Gly Thr Cys Thr Val Gln Lys Leu Ala His Gln
1               5                   10                  15

Ile Tyr Gln Phe Thr Asp Lys Asp Lys Gln Asp Ser Ala Pro Val Asp
                20                  25                  30

Pro Ser Ser Pro His Ser Tyr
            35

<210> SEQ ID NO 27
<211> LENGTH: 40
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (40)..(40)
<223> OTHER INFORMATION: AMIDATION

<400> SEQUENCE: 27

Lys Gly Cys Val Leu Gly Thr Cys Gln Val Gln Asn Leu Ser His Arg
1               5                   10                  15

Leu Trp Gln Leu Met Gly Pro Ala Gly Arg Gln Asp Ser Ala Pro Val
                20                  25                  30

Asp Pro Ser Ser Pro His Ser Tyr
            35                  40

<210> SEQ ID NO 28
<211> LENGTH: 36
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (36)..(36)
<223> OTHER INFORMATION: AMIDATION

<400> SEQUENCE: 28

Lys Gly Cys Arg Phe Gly Thr Cys Thr Val Gln Lys Leu Ala His Gln
1               5                   10                  15

Ile Tyr Gln Phe Thr Asp Lys Asp Ser Ala Pro Val Asp Pro Ser Ser
                20                  25                  30

Pro His Ser Tyr
            35

<210> SEQ ID NO 29
<211> LENGTH: 39
<212> TYPE: PRT
<213> ORGANISM: Artificial sequence
```

<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue is modified with 11-amino-3,6,9-
trioxaundecanoic acid
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (39)..(39)
<223> OTHER INFORMATION: AMIDATION

<400> SEQUENCE: 29

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Ala Pro Arg Ser
            20                  25                  30

Lys Ile Ser Pro Gln Gly Tyr
        35

<210> SEQ ID NO 30
<211> LENGTH: 46
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue is modified with 11-amino-3,6,9-
trioxaundecanoic acid
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (46)..(46)
<223> OTHER INFORMATION: AMIDATION

<400> SEQUENCE: 30

Lys Thr Lys Lys Thr Leu Arg Thr Gly Cys Arg Phe Gly Thr Cys Thr
1               5                   10                  15

Val Gln Lys Leu Ala His Gln Ile Tyr Gln Phe Thr Asp Lys Asp Lys
            20                  25                  30

Asp Asn Val Ala Pro Arg Ser Lys Ile Ser Pro Gln Gly Tyr
            35                  40                  45

<210> SEQ ID NO 31
<211> LENGTH: 36
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue is modified with 11-amino-3,6,9-
trioxaundecanoic acid
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (36)..(36)
<223> OTHER INFORMATION: AMIDATION -continued

```
<400> SEQUENCE: 31

Lys Gly Cys Arg Phe Gly Thr Cys Thr Val Gln Lys Leu Ala His Gln
1               5                   10                  15

Ile Tyr Gln Phe Thr Asp Lys Asp Lys Asp Asn Val Asp Pro Ser Ser
                20                  25                  30

Pro His Ser Tyr
            35

<210> SEQ ID NO 32
<211> LENGTH: 36
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue is modified with 11-amino-3,6,9-
      trioxaundecanoic acid
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (36)..(36)
<223> OTHER INFORMATION: AMIDATION

<400> SEQUENCE: 32

Lys Gly Cys Arg Phe Gly Thr Cys Thr Val Gln Lys Leu Ala His Gln
1               5                   10                  15

Ile Tyr Gln Phe Thr Asp Lys Asp Val Ala Pro Arg Ser Lys Ile Ser
                20                  25                  30

Pro Gln Gly Tyr
            35

<210> SEQ ID NO 33
<211> LENGTH: 36
<212> TYPE: PRT
<213> ORGANISM: Artificial sequence
<220> FEATURE:
<223> OTHER INFORMATION: Synthetic polypeptide
<220> FEATURE:
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (36)..(36)
<223> OTHER INFORMATION: AMIDATION

<400> SEQUENCE: 33

Lys Gly Cys Arg Phe Gly Thr Cys Thr Val Gln Lys Leu Ala His Gln
1               5                   10                  15

Ile Tyr Gln Phe Thr Asp Lys Asp Val Ala Pro Arg Ser Lys Ile Ser
                20                  25                  30

Pro Gln Gly Tyr
            35

<210> SEQ ID NO 34
<211> LENGTH: 35
<212> TYPE: PRT
<213> ORGANISM: Artificial sequence
<220> FEATURE:
<223> OTHER INFORMATION: Synthetic polypeptide
<220> FEATURE:
```

```
<221> NAME/KEY: LIPID
<222> LOCATION: (1)..(1)
<223> OTHER INFORMATION: PALMITATE
<220> FEATURE:
<221> NAME/KEY: MOD_RES
<222> LOCATION: (35)..(35)
<223> OTHER INFORMATION: AMIDATION

<400> SEQUENCE: 34

Lys Gly Cys Arg Phe Gly Thr Cys Thr Val Gln Lys Leu Ala His Gln
1               5                   10                  15

Ile Tyr Gln Phe Thr Asp Lys Asp Ala Pro Val Asp Pro Ser Ser Pro
            20                  25                  30

His Ser Tyr
        35
```